US010823735B2

(12) United States Patent
Khoo et al.

(10) Patent No.: US 10,823,735 B2
(45) Date of Patent: Nov. 3, 2020

(54) MONOCLONAL ANTIBODY FOR PREDICTING TAMOXIFEN RESPONSE IN BREAST CANCER PATIENTS

(71) Applicant: The University of Hong Kong, Hong Kong (CN)

(72) Inventors: Ui Soon Khoo, Hong Kong (CN); Chun Jade Gong, Hong Kong (CN); Kin Wah Terence Lee, Hong Kong (CN)

(73) Assignee: THE UNIVERSITY OF HONG KONG, Hong Kong (CN)

( * ) Notice: Subject to any disclaimer, the term of this patent is extended or adjusted under 35 U.S.C. 154(b) by 0 days.

(21) Appl. No.: 15/756,824

(22) PCT Filed: Aug. 29, 2016

(86) PCT No.: PCT/CN2016/097131
§ 371 (c)(1),
(2) Date: Mar. 1, 2018

(87) PCT Pub. No.: WO2017/036369
PCT Pub. Date: Mar. 9, 2017

(65) Prior Publication Data

US 2018/0246107 A1 Aug. 30, 2018

Related U.S. Application Data

(60) Provisional application No. 62/213,661, filed on Sep. 3, 2015.

(51) Int. Cl.

| | |
|---|---|
| ***C07K 16/18*** | (2006.01) |
| ***C07K 16/22*** | (2006.01) |
| ***G01N 33/574*** | (2006.01) |
| ***C07K 14/47*** | (2006.01) |
| ***G01N 33/577*** | (2006.01) |
| ***C12N 5/12*** | (2006.01) |

(52) U.S. Cl.
CPC ....... *G01N 33/57415* (2013.01); *C07K 14/47* (2013.01); *C07K 16/18* (2013.01); *C07K 16/22* (2013.01); *C12N 5/12* (2013.01); *G01N 33/574* (2013.01); *G01N 33/577* (2013.01); *C07K 2317/31* (2013.01); *C07K 2317/34* (2013.01); *C07K 2317/515* (2013.01); *C07K 2317/55* (2013.01); *C07K 2317/565* (2013.01); *G01N 2800/52* (2013.01); *G01N 2800/54* (2013.01)

(58) Field of Classification Search
None
See application file for complete search history.

(56) References Cited

FOREIGN PATENT DOCUMENTS

WO WO-2012/055565 A1 5/2012
WO WO 2014/160499 * 10/2014

OTHER PUBLICATIONS

Maynard et al (Annual Review Biomedical Engineering, 2000, 2:339-376).*
International Search Report dated Nov. 19, 2016 in International Application No. PCT/CN2016/097131, filed Aug. 29, 2016.
Zhang, L. et al., "SpliceArray Profiling of Breast Cancer Reveals a Novel Variant of NCOR2/SMRT That Is Associated with Tamoxifen Resistance and Control of ERα Transcriptional Activity", *Cancer Research*, Jan. 1, 2013, 73(1):246-255, 2012 American Association for Cancer Research.
Cheng, X. et al., "G Protein Pathway Suppressor 2 (GPS2) Is a Transcriptional Corepressor Important for Estrogen Receptor Alpha-Mediated Transcriptional Regulation", *Journal of Biological Chemistry*, Oct. 26, 2009, 1-25, The American Society for Biochemistry and Molecular Biology, Inc.
Coller, J.K. et al., "The influence of CYP2B6, CYP2C9 and CYP2D6 genotypes on the formation of the potent antioestrogen Z-4-hydroxy-tamoxifen in human liver", *British Journal of Clinical Pharmacology*, 2002, 54:157-167, Blackwell Science Ltd.
De Souza, J.A. et al., "CYP2D6 Genotyping and Tamoxifen: An Unfinished Story in the Quest for Personalized Medicine", *Seminars in Oncology*, Apr. 2011, 38(2):263-273, Elsevier Inc.
Detre, S. et al., "A "quickscore" method for immunohistochemical semiquantitation: validation for oestrogen receptor in breast carcinomas", *Journal of Clinical Pathology*, 1995, 48:876-878.
Dezentjé, V.O. et al., "Clinical Implications of CYP2D6 Genotyping in Tamoxifen Treatment for Breast Cancer", *Clinical Cancer Research*, Jan. 1, 2009, 15(1):15-21, American Association for Cancer Research.
Hoskins, J.M. et al., "CYP2D6 and tamoxifen: DNA matters in breast cancer", *Nature Reviews Cancer*, Aug. 2009, 9:576-586, Macmillan Publishers Limited.
Ring, A. et al., "Mechanisms of tamoxifen resistance", *Endocrine-Related Cancer*, 2004, 11:643-658, Society for Endocrinology, Great Britain.
Sharma, D. et al., "Restoration of Tamoxifen Sensitivity in Estrogen Receptor-Negative Breast Cancer Cells: Tamoxifen-Bound Reactivated ER Recruits Distinctive Corepressor Complexes", *Cancer Research*, Jun. 15, 2006, 66(12):6370-6378, American Association for Cancer Research.

(Continued)

*Primary Examiner* — Laura B Goddard
(74) *Attorney, Agent, or Firm* — Saliwanchik, Lloyd & Eisenschenk

(57) ABSTRACT

Provided are a monoclonal antibody specific for BQ323636.1, and its use for prediction of tamoxifen resistance in breast cancer patients.

17 Claims, 15 Drawing Sheets
(4 of 15 Drawing Sheet(s) Filed in Color)
Specification includes a Sequence Listing.

(56) References Cited

OTHER PUBLICATIONS

Wong, L.C. et al., "AIBI gene amplification and the instability of polyQ encoding sequence in breast cancer cell lines", *BMC Cancer*, May 2, 2006, 6(111):1-8, Wong et al, BioMed Central Ltd.
Zhang, X. et al., "TBLRI regulates the expression of nuclear hormone receptor co-repressors", *BMC Cell Biology*, Aug. 7, 2006, 7(31):1-17, Zhang et al, BioMed Central Ltd.
Zhang, L., "Splice variant profiling in relation to tamoxifen resistance in breast cancer", *European Journal of Cancer Supplements*, Aug. 31, 2010, 8(5):1-158, The University of Hong Kong, Hong Kong SAR.
Dehal, S.S. et al., "CYP2D6 Catalyzes Tamoxifen 4-Hydroxylation in Human Liver", *Cancer Research*, Aug. 15, 1997, 57:3402-3406, American Association for Cancer Research.
Lefranc, M. et al., "IMGT, the international ImMunoGeneTics database", *Nucleic Acids Research*, 1999, 27(1):209-212, Oxford University Press.
Venter, J.C. et al., "GenBank: EAW98453", *GenBank*, Mar. 23, 2015, Sequence Listing.

* cited by examiner

Figure 1

(A) MSGSTQPVAQTWRATEPRYPPHSLSYPVQIARTHTDVGLLEYQHH
SRDYASHLSPGSIIQPQRRRPSLLSEFQPGNERSQELHLRPESHSYLP
ELGKSEMEFIESKRPRLELLPDPLLRPSPLLATGQPAGSEDLTKDRSLT
GKLEPVSPPSPPHTDPELELVPPRLSKEELIQNMDRVDREITMVEQ
QISKLKKKQQQLEEEAAKPPEPEKPVSPPPIESKHRSLVQIIYDENRK
KAEAAHRILEGLGPQVELPLYNQPSDTRQYHENIKINQAMRKKLILY
FKRRNHARKQWEQKFCQRYDQLMEAWEKKVERIENNPRRRAKES
KVREYYEKQFPEIRKQRELQERMQRTWRSRCASWP

BQ-antibody isotope

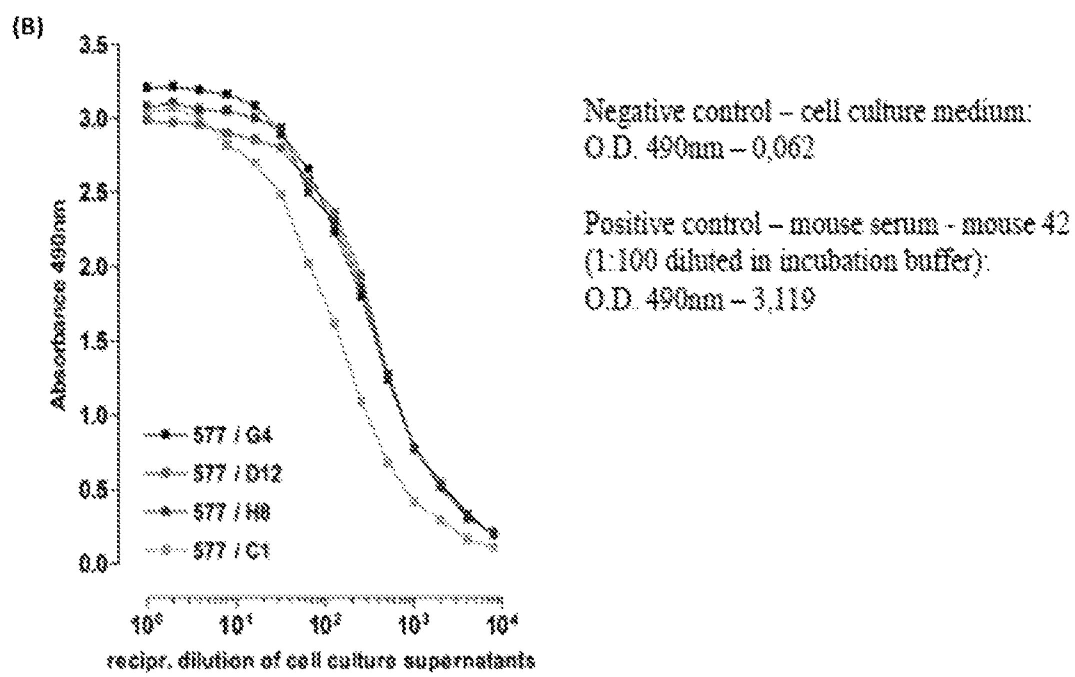

(A)
148kDa
98kDa
64kDa
50kDa
36kDa
22kDa
(G4)
(C1)
(H8)
(D12)
(B)
IgG G4 D12
64kDa
50kDa
36kDa
22kDa
BQ
(C)
D12 1:50
AK47
(D)
D12 1:50

Figure 4
(A)
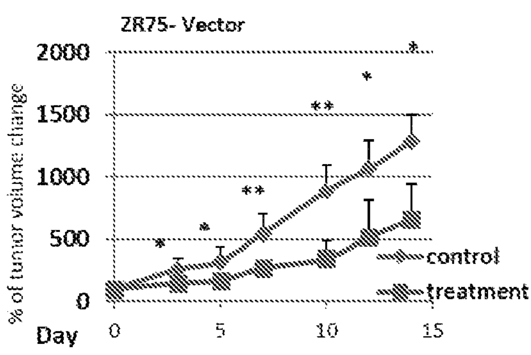
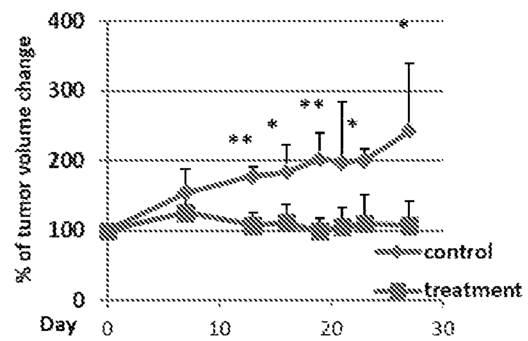
(B)
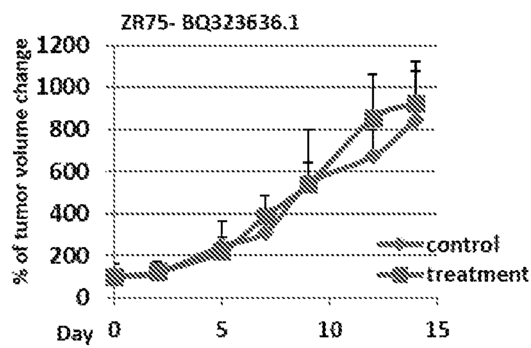
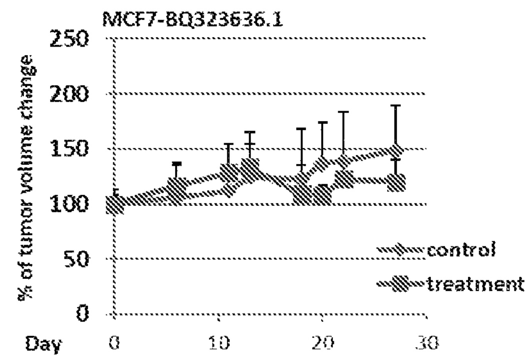
*, p<0.05, ** p<0.01

Figure 5

(A) BQ_H Score Tam resistance Crosstabulation

Count

| | | Tam resistant | | |
|---|---|---|---|---|
| | | No | Yes | Total |
| BQ_H score | low | 151 | 68 | 219 |
| | high | 56 | 72 | 128 |
| Total | | 207 | 140 | 347 |

Chi-Square Tests

| | Value | df | Asymp. Sig. (2-sided) | Exact Sig. (2-sided) | Exact Sig. (1-sided) |
|---|---|---|---|---|---|
| Pearson Chi-Square | 21.315[a] | 1 | 3.90E-06 | | |
| Continuity Correction[b] | 20.280 | 1 | 3.90E-06 | | |
| Likelihood Ratio | 21.244 | 1 | 3.90E-06 | | |
| Fisher's Exact Test | | | 3.90E-06 | 5.18E-06 | 3.47E-06 |
| Linear-by-Linear Association | 21.253 | 1 | 3.90E-06 | | |
| N of Valid Cases | 347 | | | | |

a. 0 cells (0.0%) have expected count less than 5. The minimum expected count is 51.64.
b. Computed only for a 2x2 table

(B)

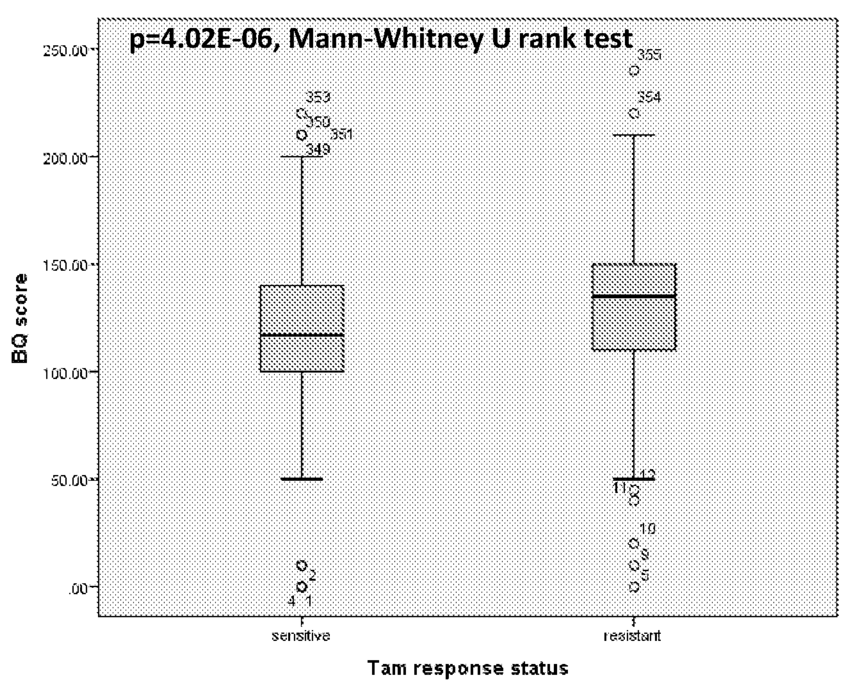

Figure 6

(A) BQ_H Score Disease Relapse Crosstabulation

Count

| | | Disease Relapse | | |
|---|---|---|---|---|
| | | No | Yes | Total |
| BQ_H Score | Low | 159 | 59 | 218 |
| | High | 68 | 58 | 126 |
| Total | | 227 | 117 | 344 |

Chi-Square Tests

| | Value | df | Asymp. Sig. (2-sided) | Exact Sig. (2-sided) | Exact Sig. (1-sided) |
|---|---|---|---|---|---|
| Pearson Chi-Square | 12.800[a] | 1 | 3.47E-04 | | |
| Continuity Correction[b] | 11.968 | 1 | 5.41E-04 | | |
| Likelihood Ratio | 12.628 | 1 | 3.80E-04 | | |
| Fisher's Exact Test | | | | 4.04E-04 | 2.93E-04 |
| Linear-by-Linear Association | 12.762 | 1 | 3.54E-04 | | |
| N of Valid Cases | 344 | | | | |

a. 0 cells (0.0%) have expected count less than 5. The minimum expected count is 42.85.
b. Computed only for a 2x2 table (B)

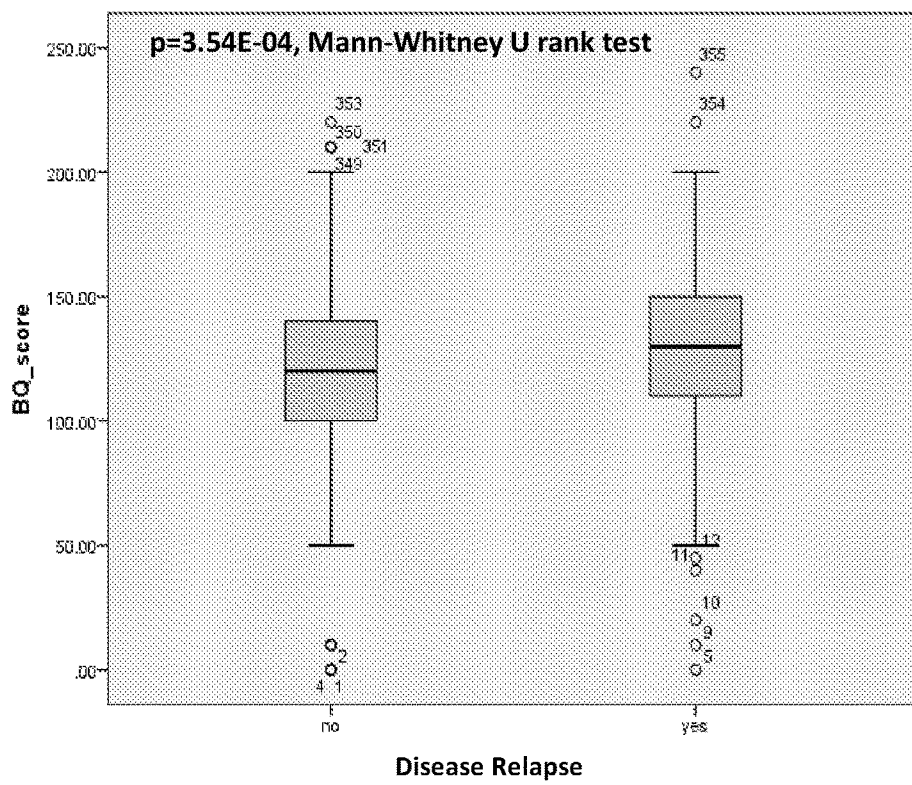

Figure 7

(A) BQ_H Score Metastasis Crosstabulation

Count

| | | Metastasis | | Total |
|---|---|---|---|---|
| | | No | Yes | |
| BQ_H Score | Low | 163 | 57 | 220 |
| | High | 64 | 67 | 131 |
| Total | | 227 | 124 | 351 |

Chi-Square Tests

| | Value | df | Asymp. Sig. (2-sided) | Exact Sig. (2-sided) | Exact Sig. (1-sided) |
|---|---|---|---|---|---|
| Pearson Chi-Square | 22.887[a] | 1 | 1.72E-06 | | |
| Continuity Correction[b] | 21.796 | 1 | 3.03E-06 | | |
| Likelihood Ratio | 22.653 | 1 | 1.94E-06 | | |
| Fisher's Exact Test | | | | 3.21E-06 | 1.70E-06 |
| Linear-by-Linear Association | 22.822 | 1 | 1.78E-06 | | |
| N of Valid Cases | 351 | | | | |

a. 0 cells (0.0%) have expected count less than 5. The minimum expected count is 46.28.
b. Computed only for a 2x2 table (B)

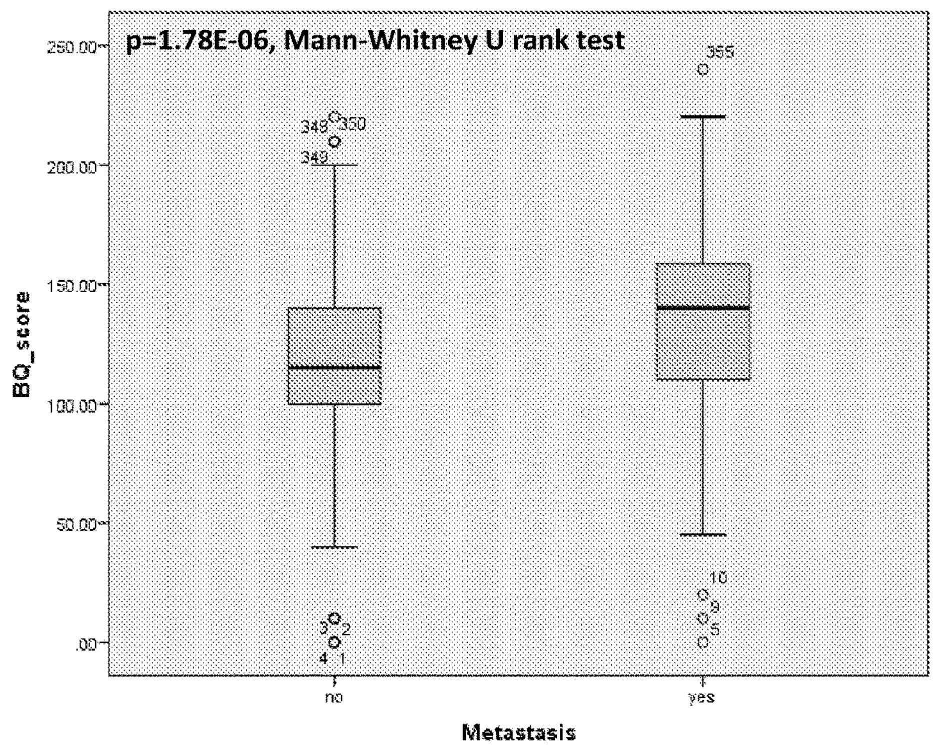

Figure 8
(A)
| Clinical parameter | Status | Sample size no (%) |
|---|---|---|
| Patients | Received Tamoxifen | 355 |
| Tumor size | <3cm | 272 (76.6%) |
| | ≥3cm | 55 (15.49%) |
| | Missing | 28 (7.89%) |
| Tumor grade | 1 and 2 | 157 (44.22%) |
| | 3 | 190 (53.5%) |
| | Missing | 8 (2.25%) |
| Lymph node involvment | Yes | 49 (13.8%) |
| | No | 35 (9.86%) |
| | Missing | 271 (76.34%) |
| PR status | Positive | 237 (66.76%) |
| | Negative | 90 (25.35%) |
| | Missing | 28 (7.89%) |
(B) Overall survival
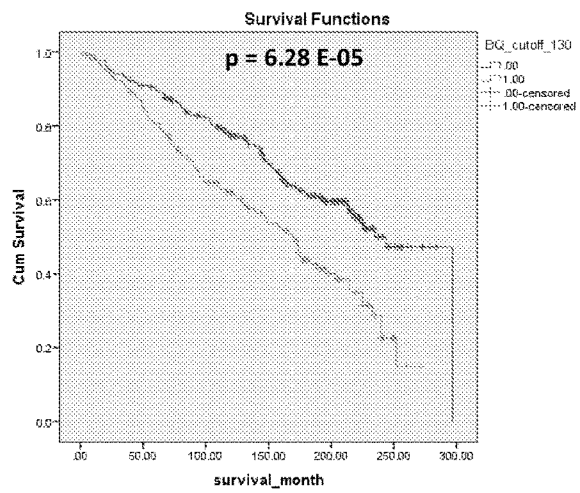
(C) Disease-specific survival
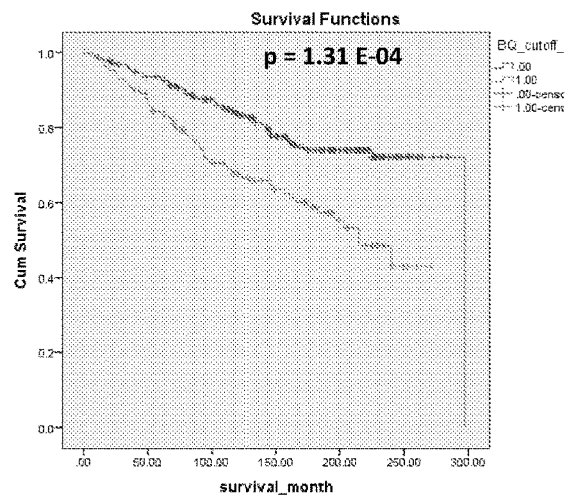

Figure 9

(A) Cox regression analyses of Overall Survivial

| Clinical-pathological parameters | Univariate analysis | | multivariate analysis | |
|---|---|---|---|---|
| | RR (95% CI) | *p* | RR (95% CI) | *p* |
| Age (n=355) | 2.005 (1.384, 2.904) | 0.000 | 1.907 (1.256, 2.893) | 0.002 |
| T-stage (n=355) | 2.838 (1.728, 4.663) | 0.000 | 3.232 (1.893, 5.518) | 0.000 |
| Lymph-node involvement | 1.325 (0.61, 2.88) | 0.477 | | |
| Tumor-Grade | 1.33 (0.971, 1.822) | 0.075 | 1.658 (1.159, 2.372) | 0.006 |
| PR status | 0.635 (0.45, 0.895) | 0.009 | 0.667 (0.467, 0.955) | 0.027 |
| HER2 status | 1.329 (0.819, 2.156) | 0.249 | | |
| BQ nucleus score | 1.842 (1.362, 2.517) | 0.000 | 2.408 (1.684, 3.445) | 0.000 |

(B) Cox regression analyses of disease-specific Survivial

| Clinical-pathological parameters | Univariate analysis | | multivariate analysis | |
|---|---|---|---|---|
| | RR (95% CI) | *p* | RR (95% CI) | *p* |
| Age (n=375) | 1.319 (0.861, 2.022) | 0.204 | | |
| T-stage (n=375) | 3.554 (2.039, 6.196) | 0.000 | 3.718 (2.025, 6.829) | 0.000 |
| Lymph-node involvement | 1.834 (0.622, 5.412) | 0.272 | | |
| Tumor-Grade | 1.677 (1.114, 2.525) | 0.013 | 1.943 (1.228, 3.075) | 0.005 |
| PR status | 0.519 (0.343, 0.783) | 0.002 | 0.539 (0.345, 0.844) | 0.007 |
| HER2 status | 1.683 (0.982, 2.884) | 0.058 | 1.939 (1.050, 3.58) | 0.034 |
| BQ nucleus score | 2.099 (1.423, 3.097) | 0.000 | 3.2 (2.025, 5.056) | 0.000 |

Figure 10
(A)ZR75
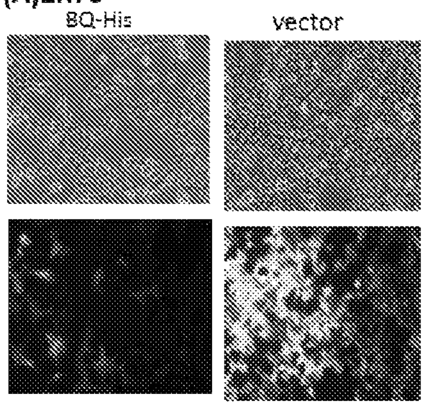
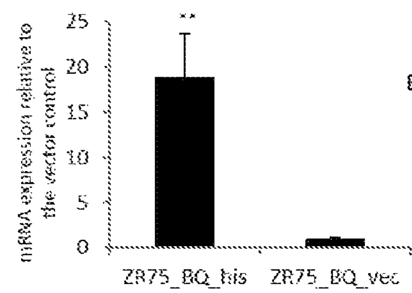
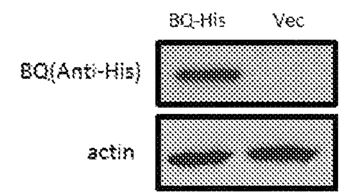
(B) MCF7
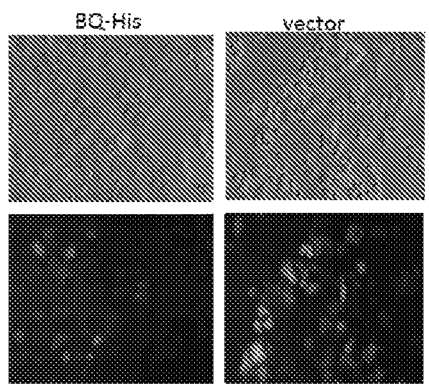
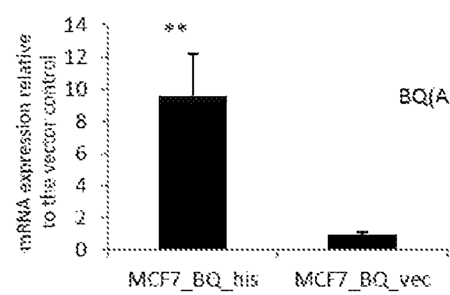
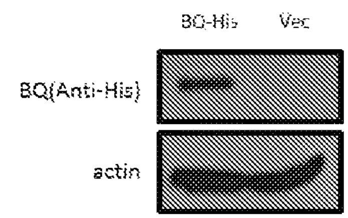

Figure 12

Heavy Chain $V_H$ Amino Acid Sequence Alignment:

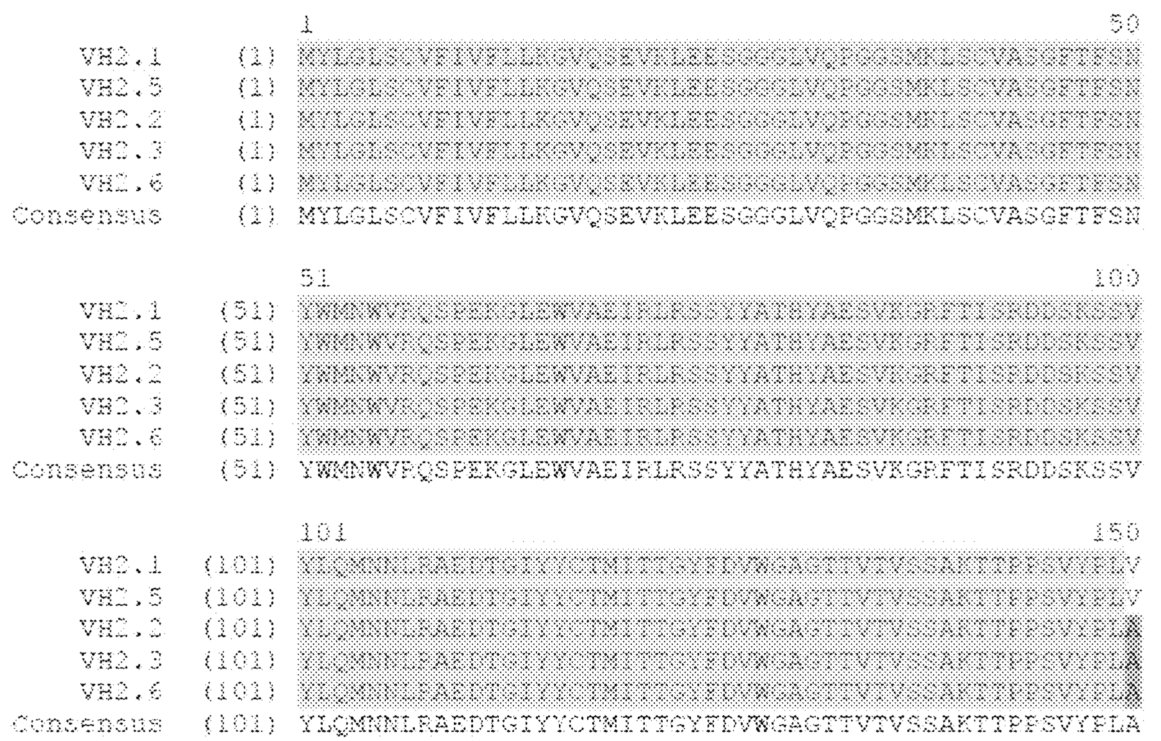

Key to amino acid shading:

Black — non-similar residues

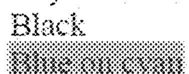
Blue on cyan — consensus residue derived from a block of residues at a given position Black on green — residues similar in structure to consensus residue or each other when no consensus found Red on yellow — consensus residue derived from a completely conserved residue at a given position Green — residue weakly similar to consensus residue at given position

Figure 13

Light Chain $V_L$ Amino Acid Sequence Alignment:

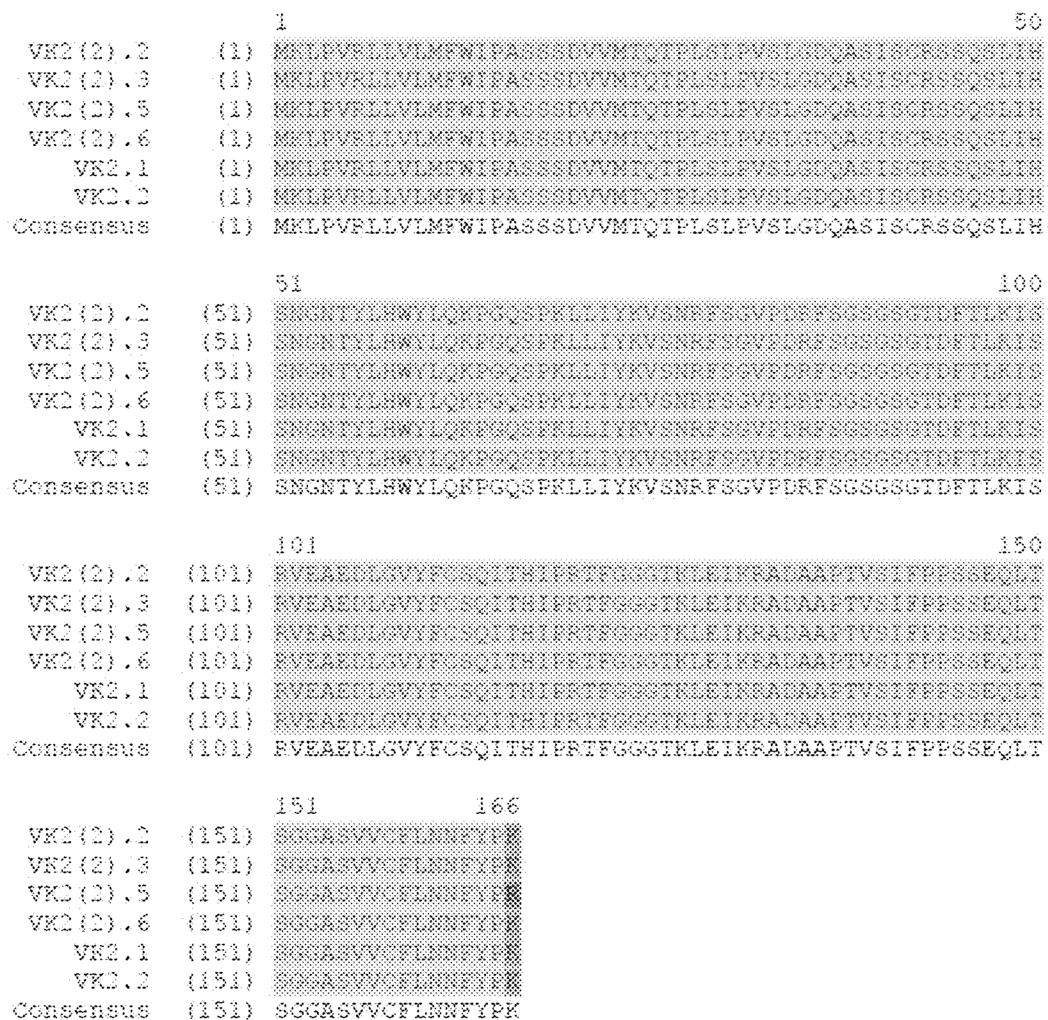

Key to amino acid shading:

| | |
|---|---|
| Black | non-similar residues |
| Blue on cyan | consensus residue derived from a block of residues at a given position |
| Black on green | residues similar in structure to consensus residue or each other when no consensus found |
| Red on yellow | consensus residue derived from a completely conserved residue at a given position |
| Green | residue weakly similar to consensus residue at given position |

Key to amino acid shading:

Blue shaded circles are hydrophobic (non-polar) residues in frameworks 1-3 at sites that are hydrophobic in the majority of antibodies.
Yellow shaded circles are proline residues
Squares are key residues at the start and end of the CDR
Red amino acids in the framework are structurally conserved amino acids Key to amino acid shading:

Blue shaded circles are hydrophobic (non-polar) residues in frameworks 1-3 at sites that are hydrophobic in the majority of antibodies.
Yellow shaded circles are proline residues
Squares are key residues at the start and end of the CDR
Red amino acids in the framework are structurally conserved amino acids

MONOCLONAL ANTIBODY FOR PREDICTING TAMOXIFEN RESPONSE IN BREAST CANCER PATIENTS

CROSS-REFERENCE TO RELATED APPLICATIONS

This application is the U.S. national stage application of International Patent Application No. PCT/CN2016/097131, filed Aug. 29, 2016, which claims the benefit of U.S. Provisional Application No. 62/213,661, filed Sep. 3, 2015, the disclosures of each of which are incorporated herein by reference in their entirety.

BACKGROUND OF THE INVENTION

Breast cancer is the most common type of malignancy affecting women worldwide. Estrogen receptor (ER) signaling pathway is a fundamental pro-proliferative pathway in the context of breast cancer. Upon its activation by binding with estrogen, ER activates target gene transcription and cell growth either directly through its genomic pathway or indirectly through non-genomic pathway that involves the PI3K/AKT pathway.

About 70% of breast cancer patients express estrogen receptor alpha (ERα) and can be treated with endocrine therapy. Tamoxifen is a selective estrogen receptor modulator (SERM) that acts as antagonist of estrogen in the context of breast and is the most commonly prescribed anti-estrogen drug to ER+ patients for prevention of breast cancer relapse or metastasis. Binding of tamoxifen to ER triggers the recruitment of nuclear co-repressor 2 (NCOR2, also known as SMRT) as well as other co-repressors such as GPS2, TBLR1, HDAC3 etc., and suppresses pro-proliferative ER signaling pathway (Sharma, Saxena et al. 2006, Zhang, Chang et al. 2006, Cheng and Kao 2009). Despite the relative safe and significant anti-neoplastic activities of tamoxifen in preventing disease relapse and improving patients' survival, resistance is an outstanding issue with up to 50% of non-responding patients, and many of the initial responders experience relapse (Ring and Dowsett 2004).

The mechanisms underlying tamoxifen resistance have been extensively studied but not yet well understood. Resistance might arise from one or more of the factors mentioned: (a) aberrant tamoxifen metabolism that affects its bioavailability; (b) dysregulation of growth factor receptor pathways and their downstream targets; (c) altered expression/function of co-regulators; (d) loss of estrogen receptor expression or function; etc.

There has been no available robust biomarker to predict the response towards tamoxifen treatment in breast cancer patients. Therefore, almost all the patients with positive ERα status will be prescribed with tamoxifen. Some of patients are resistant to this drug, but by the time the clinicians realize that the drug has failed, the cancer has already spread and metastasized.

In 2006, the US Food and Drug Administration (FDA) recommended including information on CYP2D6 genotypes and their potential effect on patient outcomes in the label for tamoxifen, but a consensus on whether genotyping should be required or considered optional was not reached (de Souza and Olopade 2011). Since then, many more clinical studies addressing the relationship between CYP2D6 and tamoxifen resistance have been published, but the results have been inconsistent and conflicting. CYP2D6 is a metabolic enzyme that catalyzes 4-hydroxylation of tamoxifen (Dehal and Kupfer 1997, Coller, Krebsfaenger et al. 2002). In terms of mortality, some studies showed that the CYP2D6 genotype is associated with shorter relapse free survival and disease-free survival while others could not find such associations (Dezentje, Guchelaar et al. 2009, Hoskins, Carey et al. 2009). Another fourteen studies have been reported on the association between CYP2D6 and the disease recurrence, but the majority of them did not find statistically significant relationships. Therefore, there is not enough solid data to justify the implementation of individual CYP2D6 genotyping for adjuvant treatment of breast cancer, and it is still questioned whether CYP2D6 can serve as a robust biomarker for predicting tamoxifen resistance.

BRIEF SUMMARY OF THE INVENTION

The present invention relates generally to monoclonal antibodies specific to a splice variant of NCOR2, named BQ323636.1, BQ323636.1 having the sequence of SEQ ID NO: 1, and their use as predictive for tamoxifen response in estrogen receptor positive breast cancer patients.

In one aspect, the present invention provides an antibody that binds a splice variant of NCOR2, wherein the splice variant is characterized by an exon 11 deletion during mRNA splicing, resulting in an early translation stop codon and truncated protein product. The splice variant has the sequence of SEQ ID NO: 1.

In some embodiments, the antibody binds an epitope of NCOR2 with the sequence of QRTWRSRCASWP (SEQ ID NO: 2). In some embodiments, the antibody is a chimeric, human, or humanized antibody. In some embodiments, the antibody is an antibody fragment selected from Fab, Fab', Fab'-SH, F (ab') 2, Fv, diabodies, single-chain antibody fragment, or a multispecific antibody comprising multiple different antibody fragments. In some embodiments, the antibody is conjugated or covalently bound to a detectable moiety.

In another aspect, the present invention provides an antibody obtained by chimerizing or humanizing an antibody that binds a splice variant of NCOR2, wherein the splice variant is characterized by an exon 11 deletion during mRNA splicing resulting in an early translation stop codon and truncated protein product.

In another aspect, the present invention provides a kit comprising the antibody that binds a splice variant of NCOR2, wherein the splice variant is characterized by an exon 11 deletion during mRNA splicing resulting in an early translation stop codon and truncated protein product, optionally further comprising a labeled secondary antibody that specifically recognizes the antibody of any one of the above claims.

In another aspect, the present invention provides a hybridoma or recombinant host cell producing an antibody that binds a splice variant of NCOR2, wherein the splice variant is characterized by an exon 11 deletion during mRNA splicing resulting in an early translation stop codon and truncated protein product.

In another aspect, the present invention provides methods of determining tamoxifen resistance in subjects with cancer, comprising:

(a) obtaining a tumor sample from the subject;

(b) determining in the sample a level of expression for a splice variant of NCOR2, wherein the splice variant is characterized by an exon 11 deletion during mRNA splicing that results in an early translation stop codon and truncated protein product;

(c) comparing the expression level in (b) to a level of expression in a normal control, wherein overexpression of the splice variant of NCOR2, with respect to the control, indicates that the cancer is tamoxifen resistant. In some embodiments, the splice variant has the sequence of SEQ ID NO: 1.

In some embodiments, the comparing step of the methods of the present invention comprises contacting the sample with an antibody that specifically recognizes an epitope of NCOR2 with the sequence of SEQ ID NO: 2; and detecting the complex between the antibody and the splice variant of NCOR2. In some embodiments, the splice variant of NCOR2 is contacted with an antibody that specifically recognizes the splice variant of NCOR2 in an immunoassay selected from the group consisting of radioimmunoassay, western blot assay, immunofluorescent assay, enzyme immunoassay, immunoprecipitation, chemiluminescent assay, immunohistochemical assay, dot blot assay, and slot blot assay.

In another aspect, the present invention provides methods of determining whether a tamoxifen-treated subject is at risk of cancer relapse, or at risk for metastasis, comprising:

(a) obtaining a tumor sample from the subject;

(b) determining in the sample a level of expression for a splice variant of NCOR2 having the sequence of SEQ ID NO: 1, wherein the splice variant is characterized by an exon 11 deletion during mRNA splicing resulting in an early translation stop codon and truncated protein product;

(c) comparing the expression level in (b) to a level of expression in a normal control, wherein overexpression of the splice variant of NCOR2, with respect to the control, indicates that the subject is at risk of cancer relapse, or is at risk for metastasis.

In some embodiments of the methods provided, the subject is a human. In some embodiments of the methods provided, the cancer is breast cancer.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1(A) shows the full peptide sequence of BQ323636.1 (SEQ ID NO: 1) highlighting the epitope (SEQ ID NO: 2) of BQ323636.1-specific monoclonal antibody in red. FIG. 1(B) shows a graph of the four clones (C1, D12, G4, H8) with highest titer of antigen specific antibody production selected with ELISA applied to assess the antigen-antibody specific binding.

FIG. 4 indicates that BQ323636.1 overexpression confers resistance to tamoxifen in vivo. (A) The control cell lines, ZR75-vector and MCF7-vector, which are originally tamoxifen sensitive, responded well to tamxoifen treatment. (B) Both BQ323636.1 over-expressing cell lines, ZR75-BQ32363.61 and MCF7-BQ323636.1, were resistant to the tamoxifen treatment, as there was no change of tumor growth compared between treatment and control group.

FIG. 5 indicates the predictive values of BQ323636.1 for tamoxifen resistance using immunohistochemical staining on tissue microarray constructed from 355 cases of archived breast cancer patients' paraffin blocks. For patients who have received tamoxifen treatment, (A) Nuclear BQ323636.1 overexpression is significantly associated with tamoxifen resistance (defined as patients who received tamoxifen treatment and subsequently developed disease relapse or metastasis) by Chi-square test ($p=3.90\times10^{-6}$). (B) Nuclear BQ323636.1 was significantly higher in patients who were later found to be tamoxifen resistant (Mann-Whitney U Rank test, $p=4.02\times10^{-6}$).

FIG. 6 shows that, (A) nuclear BQ323636.1 overexpression was significantly correlated with disease relapse (Chi-square test, $p=3.47\times10^{-4}$); (B) Nuclear BQ323636.1 was significantly higher in patients who later developed disease relapse (Mann-Whitney U Rank test, $p=3.54\times10^{-4}$).

FIG. 7 shows that, (A) nuclear BQ323636.1 overexpression was significantly correlated with cancer metastasis (Chi-square test, $p=1.72\times10^{-6}$); (B) Nuclear BQ323636.1 was significantly higher in patients who later developed metastasis (Mann-Whitney U Rank test, $p=1.78\times10^{-6}$).

FIG. 8 indicates the value of BQ323636.1 as a prognostic maker using immunohistochemical staining by Kaplan-Meier estimate. (A) Sample distribution for each clinical parameters. (B) Nuclear BQ323636.1 overexpression was significantly associated with poorer overall survival (Log-rank test, $p=6.28\times10^{-5}$). (C) Nuclear BQ323636.1 overexpression was significantly associated with poorer disease-specific survival (Log-rank test, $p=1.31\times10^{4}$)

FIG. 9 indicates the value of BQ323636.1 as a prognostic marker using immunohistochemical staining by cox-regression analysis. (A) Nuclear BQ323636.1 overexpression was significantly associated with poorer overall survival (risk ratio=1.842, p=0.000) on univariate analysis, which remained significant on multivariate analysis (risk ratio=2.41, p=0.000). (B) Nuclear BQ323636.1 overexpression was significantly associated with poorer disease-specific survival (risk ratio=2.10, p=0.000) on univariate analysis, which also remained significant on multivariate analysis (risk ratio=3.2, p=0.000).

FIG. 10 shows cell lines that were stably overexpressing BQ323636.1 ((A) ZR75-BQ323636.1 and (B) MCF 7-BQ323636.1) generated by lentiviral-based system. Transfection efficiency was monitored by the GFP signal. Overexpression of BQ323636.1 was further confirmed by western blot and qPCR.

FIG. 12 shows $V_H$ amino acid sequence alignment for the monoclonal antibody of the present invention. The sequence alignment shows $V_H$ amino acid sequences of the heavy chains of: VH2.1 (SEQ ID NO: 32), VH2.5 (SEQ ID NO: 33), VH 2.2 (SEQ ID NO: 34), VH 2.3 (SEQ ID NO: 35), VH2.6 (SEQ ID NO: 36), and the consensus $V_H$ amino acid sequence (SEQ ID NO: 3).

FIG. 13 shows $V_L$ amino acid sequence alignment for the monoclonal antibody of the present invention. The sequence alignment shows $V_L$ amino acid sequences of the light chains of: VK2 (2).2 (SEQ ID NO: 38), VK2 (2).3 (SEQ ID NO: 39), VK2 (2).5 (SEQ ID NO: 40), VK2 (2).6 (SEQ ID NO: 41), VK2.1 (SEQ ID NO: 42), VK2.2 (SEQ ID NO: 43), and the consensus $V_L$ amino acid sequence (SEQ ID NO: 44).

BRIEF DESCRIPTION OF THE SEQUENCES

Figure 2:
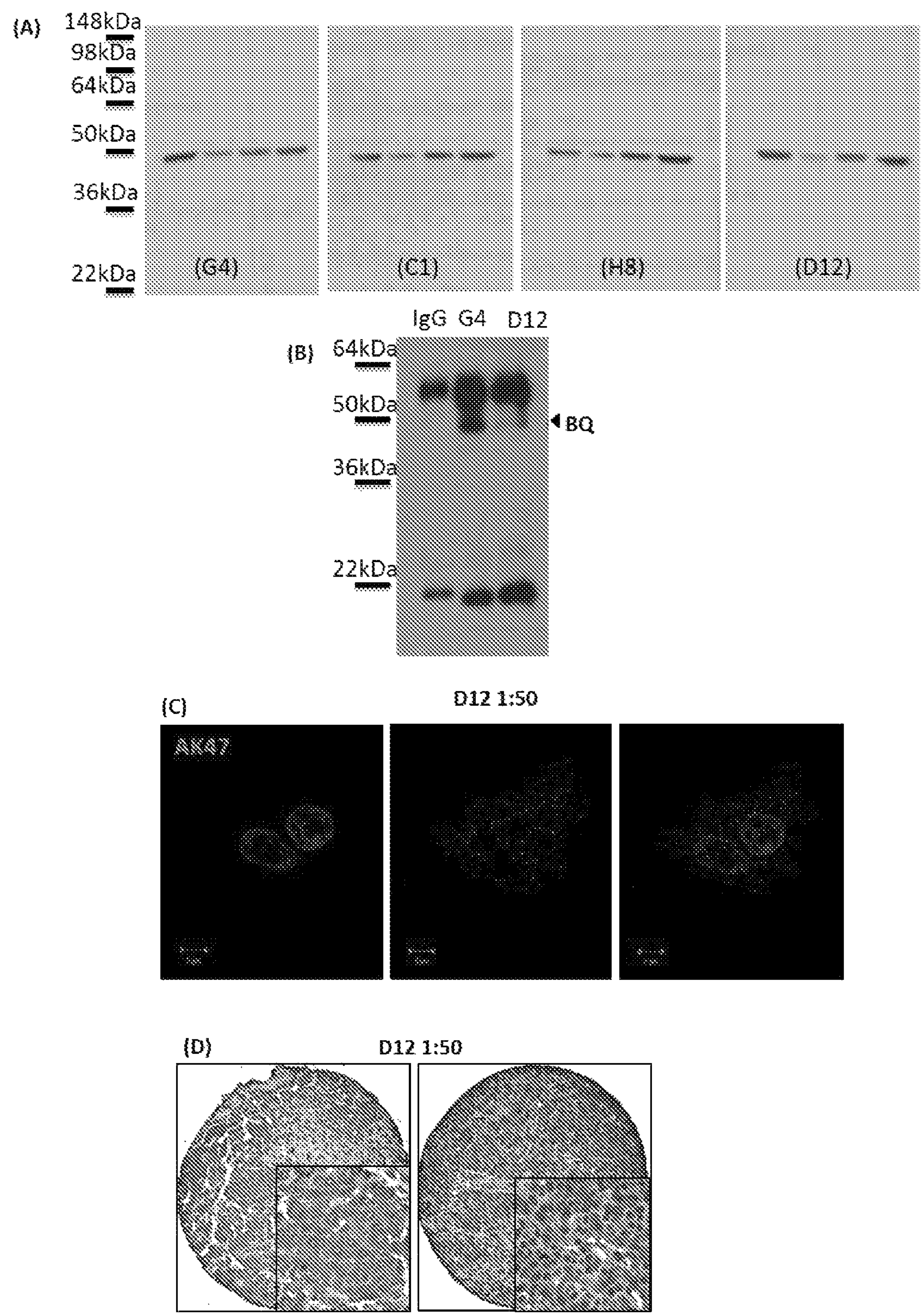
FIG. 2 shows the four clones of the anti-BQ323636.1 antibody that were tested in the application of (A) western blot, (B) immuno-precipitation, (C) immunofluorescence staining and (D) immunohistochemistry staining. Among the four clones tested, D12 and G4 showed the best performance.

SEQ ID NO: 1 is the amino acid sequence of the BQ323636.1 splice variant of NCOR2.

SEQ ID NO: 2 is the amino acid sequence of the region of the BQ323636.1 splice variant of NCOR2 bound by the antibodies of the present invention.

SEQ ID NO: 3 is the $V_H$ consensus amino acid sequence for the monoclonal antibody of the present invention.

SEQ ID NO: 4 is the amino acid sequence for VH2.1.

SEQ ID NO: 5 is the amino acid sequence for VH2.2.

SEQ ID NO: 6 is the amino acid sequence for VH2.3.

SEQ ID NO: 7 is the amino acid sequence for VH2.5.

SEQ ID NO: 8 is the amino acid sequence for VH2.6.

SEQ ID NO: 9 is the nucleic acid sequence for VH2.1.

SEQ ID NO: 10 is the nucleic acid sequence for VH2.2.

SEQ ID NO: 11 is the nucleic acid sequence for VH2.3.

SEQ ID NO: 12 is the nucleic acid sequence for VH2.5.

SEQ ID NO: 13 is the nucleic acid sequence for VH2.6.

SEQ ID NO: 14 is the amino acid sequence for VK2.1.

SEQ ID NO: 15 is the amino acid sequence for VK2.2.

SEQ ID NO: 16 is the amino acid sequence for VK2(2).2.

SEQ ID NO: 17 is the amino acid sequence for VK2(2).3.

SEQ ID NO: 18 is the amino acid sequence for VK2(2).5.

SEQ ID NO: 19 is the amino acid sequence for VK2(2).6.

SEQ ID NO: 20 is the nucleic acid sequence for VK2.1.

SEQ ID NO: 21 is the nucleic acid sequence for VK2.2.

SEQ ID NO: 22 is the nucleic acid sequence for VK2(2).2.

SEQ ID NO: 23 is the nucleic acid sequence for VK2(2).3.

SEQ ID NO: 24 is the nucleic acid sequence for VK2(2).5.

SEQ ID NO: 25 is the nucleic acid sequence for VK2(2).6.

SEQ ID NO: 26 is the amino acid sequence of the last 16 amino acids of the $V_L$ consensus amino acid sequence SEQ ID NO: 44 for the monoclonal antibody of the present invention.

SEQ ID NO: 27 is the sequence of hCDR1 of the $V_H$ of a monoclonal antibody against the peptide of SEQ ID NO: 2.

SEQ ID NO: 28 is the sequence of hCDR2 of the $V_H$ of a monoclonal antibody against the peptide of SEQ ID NO: 2.

SEQ ID NO: 29 is the sequence of hCDR3 of the $V_H$ of a monoclonal antibody against the peptide of SEQ ID NO: 2.

SEQ ID NO: 30 is the sequence of lCDR1 of the $V_L$ of a monoclonal antibody against the peptide of SEQ ID NO: 2.

SEQ ID NO: 31 is the sequence of lCDR3 of the $V_L$ of a monoclonal antibody against the peptide of SEQ ID NO: 2.

SEQ ID NO: 32 is the $V_H$ amino acid sequence for VH2.1.

SEQ ID NO: 33 is the $V_H$ amino acid sequence for VH2.5.

SEQ ID NO: 34 is the $V_H$ amino acid sequence for VH2.2.

SEQ ID NO: 35 is the $V_H$ amino acid sequence for VH2.3.

SEQ ID NO: 36 is the $V_H$ amino acid sequence for VH2.6.

SEQ ID NO: 37 is the consensus $V_H$ amino acid sequence.

SEQ ID NO: 38 is the $V_L$ amino acid sequence for VK2 (2).2.

SEQ ID NO: 39 is the $V_L$ amino acid sequence for VK2 (2).3.

SEQ ID NO: 40 is the $V_L$ amino acid sequence for VK2 (2).5.

SEQ ID NO: 41 is the $V_L$ amino acid sequence for VK2 (2).6.

SEQ ID NO: 42 is the $V_L$ amino acid sequence for VK2.1.

SEQ ID NO: 43 is the $V_L$ amino acid sequence for VK2.2.

SEQ ID NO: 44 is the consensus $V_L$ amino acid sequence.

DETAILED DESCRIPTION OF THE INVENTION

Cell culture D12 has been deposited on Jul. 2, 2015, with the Leibniz Institute DSMZ-German Collection of Microorganisms and Cell Cultures, located at Inhoffenstr. 7B, D-38124 Braunschweig, Germany, under conditions that assure that access to the cultures will be available during the pendency of this patent application to one determined by the Commissioner of Patents and Trademarks to be entitled thereto under 37 CFR 1.14 and 35 U.S.C. 122. The deposit has been assigned accession number DSM ACC3272 and will be available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least thirty (30) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

Applicants have previously identified a splice variant of NCOR2 (NCOR2 is also known as SMRT), named BQ323636.1, which is associated with tamoxifen resistance in breast cancer (Zhang L, Gong C, et al, 2013). The BQ323636.1 splice variant is characterized by skipped exon 11 during mRNA splicing, resulting in an early translation stop codon and a truncated protein product retaining only the N-terminal fragment compared to its wild-type (Zhang, Gong et al. 2013).

The present invention provides an antibody specific for BQ323636.1. The present invention also provides methods involving the use of monoclonal BQ323636.1 antibody for predicting patients' responses to tamoxifen treatment. The development of such a reliable biomarker enables appropriate alternative therapy to be given to breast cancer patients at an early stage without suffering from undesirable side effects of tamoxifen. Predicting which patients will respond to tamoxifen and which will not provide the advantageous ability to provide the correct treatment early to improve disease outcome.

In one aspect, the present invention provides an antibody that binds a splice variant of NCOR2 having the sequence of SEQ ID NO: 1, wherein the splice variant is characterized by an exon 11 deletion during mRNA splicing resulting in an early translation stop codon and truncated protein product.

In some embodiments, the antibody binds an epitope of NCOR2 with the sequence of SEQ ID NO: 2. In some embodiments, the antibody is a chimeric, human, or humanized antibody. In some embodiments, the antibody is an antibody fragment selected from Fab, Fab', Fab'-SH, F (ab') 2, Fv, diabodies, single-chain antibody fragment, or a multispecific antibody comprising multiple different antibody fragments. In some embodiments, the antibody is conjugated or covalently bound to a detectable moiety.

In another aspect, the present invention provides an antibody obtained by chimerizing or humanizing an antibody that binds a splice variant of NCOR2, wherein the splice variant is characterized by an exon 11 deletion during mRNA splicing resulting in an early translation stop codon and truncated protein product. In some embodiments, the splice variant has the sequence of SEQ ID NO: 1. In some embodiment, the antibody binds an epitope on the NCOR2 splice variant having the sequence of SEQ ID NO: 2.

The term "antibody" may be used interchangeably with the term "immunoglobulin" and is defined herein as a protein synthesized by an animal or a cell of the immune system in response to an antigen or immunogen. The term antibody as used herein also refers to fragments thereof. Antibodies are characterized by specific affinity to a site on the antigen referred to as an "antigenic determinant" or an "epitope". Antigens can be naturally occurring or artificially engineered. The immunoglobulin molecules utilized in the present invention can be of any type (e.g., IgG, IgE, IgM, IgD, IgA and IgY), class (e.g., IgA1, IgA2, IgG1, IgG2, IgG3, and IgG4) or subclass of immunoglobulin molecule.

Antibodies can include either polyclonal or monoclonal antibodies. In preferred embodiments, the antibodies of the present invention are monoclonal antibodies. In addition to intact immunoglobulin molecules, also included are fragments or polymers of those immunoglobulin molecules, and human or humanized versions of immunoglobulin molecules or fragments thereof, as long as the molecules maintain the ability to bind with an epitope of the NCOR2 splice variant. The antibodies can be tested for their desired activity using the in vitro assays described herein, or by analogous methods, after which the in vivo therapeutic and/or diagnostic activities can be confirmed and quantified according to known clinical testing methods.

The antibodies utilized in the present invention are inclusive of all species, and the antigenic target can be from any species. Most preferably, the antibodies are human antigen-binding antibodies, and fragments thereof, and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the hinge region, CH1, CH2, and/or CH3 domains. Single chain antibodies are formed by linking the heavy and light chain fragments of the Fv region via an amino acid bridge, resulting in a single chain polypeptide. Also included in the invention are antigen-binding fragments comprising any combination of variable region(s) with a hinge region, CH1, CH2, and/or CH3 domains.

The antibodies and aptamers useful in the present invention may be generated by any suitable method known in the art. Monoclonal antibodies can be prepared using any of the techniques known in the art, including the use of hybridoma, recombinant, and phage display technologies, or a combination thereof. The term "monoclonal antibody" or "mAb" as used herein is not limited to antibodies produced through hybridoma technology. The term refers to any antibody that is derived from a single clone, including any eukaryotic, prokaryotic, or phage clone, and not the method by which it is produced. Methods for producing and screening for specific antibodies using hybridoma technology are routine and well known in the art. Similarly, methods for producing and screening for specific aptamers are routine and well known in the art.

In some instances, it may be desirable to use chimeric, humanized, or human antibodies in the invention. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art and may include splicing genes from a mouse antibody molecule of appropriate antigen specificity together with genes from a human antibody molecule of appropriate biological activity. Humanized antibodies are antibody molecules from a non-human species antibody that binds the desired antigen having one or more complementarity determining regions (CDRs) from the non-human species and a framework region from a human immunoglobulin molecule. Completely human antibodies may be desirable for therapeutic treatment of human patients. Human antibodies can be made by a variety of methods known in the art.

In some embodiments, the antibody of the present invention has a $V_H$ amino acid sequence of SEQ ID NO:3 and/or a $V_L$ amino acid sequence of SEQ ID NO: 44.

In another aspect, the present invention provides a kit comprising the antibody or aptamer that binds a splice variant of NCOR2, wherein the splice variant is characterized by an exon 11 deletion during mRNA splicing resulting in an early translation stop codon and truncated protein product, optionally further comprising a labeled secondary antibody or aptamer that specifically recognizes the anti-variant-NCOR2 antibody or aptamer. The splice variant comprises the sequence of SEQ ID NO: 1.

In another aspect, the present invention provides a hybridoma or recombinant host cell producing an antibody that binds a splice variant of NCOR2, wherein the splice variant is characterized by an exon 11 deletion during mRNA splicing resulting in an early translation stop codon and truncated protein product. The splice variant comprises the sequence of SEQ ID NO: 1.

In another aspect, the present invention provides methods of determining tamoxifen resistance in subjects with cancer, comprising:

(a) obtaining a tumor sample from a subject;

(b) determining in the sample a level of expression for a splice variant of NCOR2, wherein the splice variant is characterized by an exon 11 deletion during mRNA splicing resulting in an early translation stop codon and truncated protein product;

(c) comparing the expression level in (b) to a level of expression in a normal control, wherein overexpression of the splice variant of NCOR2, with respect to the control, indicates that the cancer is tamoxifen resistant. In some embodiments, the splice variant has the sequence of SEQ ID NO: 1.

In some embodiments, the comparing step of the methods of the present invention comprises contacting the sample with an antibody or aptamer that specifically recognizes an epitope of NCOR2 with the sequence of SEQ ID NO: 2; and detecting the complex between the antibody or aptamer and the splice variant of NCOR2. In some embodiments, the splice variant of NCOR2 is contacted with an antibody that specifically recognizes the splice variant of NCOR2 in an immunoassay selected from the group consisting of radioimmunoassay, western blot assay, immunofluorescent assay, enzyme immunoassay, immunoprecipitation, chemiluminescent assay, immunohistochemical assay, dot blot assay, and slot blot assay.

In another aspect, the present invention provides methods of determining whether a tamoxifen-treated subject is at risk of cancer relapse, or at risk for metastasis, comprising:

(a) obtaining a tumor sample from the subject;

(b) determining in the sample a level of expression for a splice variant of NCOR2 having the sequence of SEQ ID NO: 1, wherein the splice variant is characterized by an exon 11 deletion during mRNA splicing resulting in an early translation stop codon and truncated protein product;

(c) comparing the expression level in (b) to a level of expression in a normal control, wherein overexpression of the splice variant of NCOR2, with respect to the control, indicates that the subject is at risk of cancer relapse, or is at risk for metastasis.

In some embodiments of the methods provided, the subject is a human. In some embodiments of the methods provided, the cancer is breast cancer.

The antibodies, or antibody fragments thereof, and aptamers particularly useful in the present invention specifically bind to an epitope comprising the amino acid sequence set forth in SEQ ID NO: 2.

Without further elaboration, it is believed that one skilled in the art can, using the preceding description, utilize the present invention to its fullest extent. The following examples are offered by way of illustration, not by way of limitation. While specific examples have been provided, the above description is illustrative and not restrictive. Anyone or more of the features of the previously described embodiments can be combined in any manner with one or more features of any other embodiments in the present invention. Furthermore, many variations of the invention will become apparent to those skilled in the art upon review of the specification.

All publications and patent documents cited in this application are incorporated by reference in pertinent part for all purposes to the same extent as if each individual publication or patent document were so individually denoted. By citation of various references in this document, Applicants do not admit any particular reference is "prior art" to their invention.

EXAMPLES

The methods, antibodies, and kits herein described are further illustrated in the following examples, which are provided by way of illustration and are not intended to be limiting. It will be appreciated that variations in proportions and alternatives in elements of the components shown will be apparent to those skilled in the art and are within the scope of embodiments of the present invention. Theoretical aspects are presented with the understanding that Applicants do not seek to be bound by the theory presented. All parts or amounts, unless otherwise specified, are by weight.

The following materials and methods were used for all the methods, antibodies, and kits exemplified herein.

Cell lines—Human breast cancer cell lines MCF7 and ZR-75-1 were purchased from American Type Culture Collection and were re-authenticated by short tandem repeat profiling (Zhang, Gong et al. 2013). MCF7 was cultured in Dulbecco's Modified Eagle's Medium supplemented with 10% FBS and 1% penicillin/streptomycin and ZR-75-1 was cultured in Improved Minimum Essential Medium (IMEM) supplemented with 5% FBS and 1% penicillin/streptomycin. LCC2 and AK-47 are the two tamoxifen resistant cell lines derived from MCF7 and ZR-75-1, respectively and were kindly provided by Dr. Robert Clarke (Georgetown University Medical School, Washington, D.C.) (Wong, Dai et al. 2006) and have been used in our previous study (Zhang, Gong et al. 2013). LCC2 and AK-47 were both cultured in IMEM supplemented with 5% charcoal-stripped FBS and 1% penicillin/streptomycin. All the cell lines used in this study have been passaged and kept fewer than 6 months after the re-authentication or thawing.

Lentiviral transfection for generation of stable cell line—For lentivirus production, early passage 293FT cells were plated at $5\times10^5$ cells/well in 6-well plates two days before transfection. The cells were grown to 80-90% confluency to perform transfection. Recombinant lentiviruses were produced by co-transfecting 293FT cells with the lentivirus expression plasmid and packaging plasmids using Lipofectamine 2000 (Invitrogen). 10 μl of Lipofectamine 2000 reagent was diluted in 250 μl plain medium and incubated at 5 minutes at room temperature. 1 μg of lentivirus expression plasmid and 2.6 μl pPACK Packaging Plasmid Mix (System Biosciences) was added to the medium with diluted Lipofectamine 2000 reagent. While this was further incubated at room temperature for 15 minutes, fresh complete medium was replaced. After the 20 minutes incubation, the DNA-Lipofectamine complexes were added to the cells and incubated overnight. On the next day, the medium with the complexes were discarded and 1 ml fresh medium containing 30% (v/v) FBS was added. At the 48 hours post transfection, the medium was harvested and centrifuged at 2000 rpm for 5 minutes at room temperature to remove cell debris. The viral supernatant was saved and stored at −80° C. until use. Target cells to be transfected were plated at $3\text{-}5\times10^5$/well in 6-well plates 24-48 hours prior to viral infection. On the day of transduction, the medium was removed and replaced with lml fresh complete medium with Polybrene (Sigma) at a final concentration of 12 μg/ml. The target cells were infected by adding 200 μl-800 μl prepared viral supernatant. After 24 hours, the culture medium was discarded and replaced with 1 ml complete medium without Polybrene. The infected target cells could be selected by adding complete medium containing 0.5-1 ug/ml puromycin (Sigma) 3-7 days post infection. GFP expression was examined by fluorescent microscopy after 3-4 days.

MTT assay—Cells were seeded at a density of $6\times10^3$ cells/well. On the day of conducting MTT assay, cells were incubated with culture medium containing 10% MTT (USB, Affymetrix, stock concentration is 5 mg/mL) at 37° C. for 4 hours. After incubation, the medium was discarded and replaced with 100 mL isopropanol with 4 mmol/L HCl and 0.1% NP-40 to dissolve the purple precipitates. Extinction of the samples was measured by the Infinite 200 microtiter plate reader (Tecan) at 570 nm with a reference wavelength at 750 nm. Background MTT readings were subtracted from the samples.

Immunoprecipitation—Cells were lysed in IP lysis buffer (0.025M Tris, 0.15M NaCl, 0.001M EDTA, 1% NP-40, 5% glycerol, pH 7.4) and pre-cleared with 30 μl of Dynabeads Protein A/G (A for rabbit antibodies, G for mouse antibodies, Invitrogen, Life Technologies, UK) by rotating at 4° C. for 4 hours. After pre-clearing, protein concentration was measured and the lysate was split into equal amount of proteins per tube and incubated with the specific primary antibody or IgG negative control (dilution 1:200) at 4° C. for O/N with gentle rotating. On the second day, 40 μl of beads were added to the mixture and incubated at 4° C. for another 4 h. After incubation, the beads were washed five times with cold PBS and boiled at 100° C. for 5 min to elute the proteins. Proteins were separated by SDS-PAGE gel electrophoresis, transferred to nitrocellulose membrane and hybridized with the antibodies same as Western blotting.

Immunofluorescence staining—Briefly, cells were fixed with 50:50 methanol:acetone (Millipore, Germany/Merck, UK) for 10 min at −20° C. Samples were then incubated overnight with the primary mouse anti-BQ (clone D12) which we have generated. Following washes with PBS, secondary goat anti-mouse IgG-FITC (1:2000, Life technologies, US) was added to the samples for an hour at 37° C. incubator. Cells were mounted with mounting medium with DAPI (Life technologies, US). Images were captured and quantified using the Carl Zeiss LSM 710 confocal laser scanning microscope and software Windows Vista, ZEN 2011 version 5.5 SP1.

Orthotopic mouse model—The cell lines mixed with Matrigel (BD Biosciences) at the ratio of 1:1 were inoculated into the abdominal mammary fat pad of the 5 to 6 week old female nude mice. When the tumor were palpable, the mice were randomized into treatment and control groups where treatment groups received daily subcutaneous injection of tamoxifen (Sigma) dissolved in peanut oil (Sigma) and the control groups received subcutaneous injection of the solvent only. Tumor sizes were measured by caliper and tumor volume was calculated as (length*width*width)/2. Tumor growth rate was expressed as the % of tumor volume change calculated as the tumor volume measured at the indicated time point normalized against the tumor volume at day 0*100%. This protocol has been reviewed and approved by Committee on the Use of Live Animals in Teaching and Research (CULATR), the University of Hong Kong (CULATR No.: 3259-14)

Tissue Microarray—Two hundred and thirty-six cases of breast cancer diagnosed between the years 1992 to 2001 with clinical follow up data were retrieved from the records of the Department of Pathology, Queen Mary Hospital of Hong Kong, with approval by the Institutional Review Board of The University of Hong Kong (UW 06-379 T/1404). Histological sections of all cases were reviewed by the pathologist, the representative paraffin tumour blocks chosen as donor block for each case and the selected areas marked for construction of tissue microarray (TMA) blocks. A total of 206 cases could be assessed and scored for BQ323636.1 staining. Of these 93 had received tamoxifen treatment and were ER positive.

We further recruited for analysis TMA sections provided by our collaborators from Nottingham University Hospital. This consisted of a large cohort of patients comprising a well-characterised consecutive series of early stage (TNM Stage I-III excluding T3 and T4 tumours) sporadic primary operable invasive breast cancers from patients (age ≤70 years) enrolled into the Nottingham Tenovus Primary Breast Carcinoma Series that presented at Nottingham City Hospital between 1989 and 1998 and managed in accordance to a uniform protocol. The study was approved by the Nottingham Research Ethics Committee 2 under the title 'Development of a molecular genetic classification of breast cancer'. The TMA sections used included 1129 breast cancer patients with pathological and clinical follow up data of over 20 years. A total of 679 cases could be assessed and scored for BQ323636.1 staining. Of these 262 had received tamoxifen treatment and were ER positive.

Hence a total of 355 Tamoxifen treated ER positive breast cancer cases from Hong Kong and the UK were used for statistical analysis.

Immunohistochemistry—The TMA sections were deparaffinized and rehydrated by incubation with xylene and decreasing concentrations of ethanol. Citrate buffer (0.01M, pH 6.0) was used for antigen retrieval. The slides were immersed into 3% $H_2O_2$/methanol for 10 min at room temperature to quench endogenous peroxidase. After rinsing in 0.05% Tween in PBS (PBST) twice, BQ323636.1 specific antibody diluted at 1:50 was added to each section and incubated at 4° C. overnight. The slides were then washed in PBST and incubated with DAKO EnVision+System-HRP-labelled Polymer Anti-Rabbit at room temperature in dark for 30 min. After washing, Chromogen DAB/substrate reagent was added onto the slides and the slides incubated for a further 6 minutes. Finally, the slides were dehydrated and mounted. Aperio ScanScope® system (Aperio technology, USA) was used to visualize and assess for BQ323636.1 expression. The TMA slides were scanned by ScanScope scanners and individual stained TMA spots were assessed in computer screen with the use of Aperio's image viewer, ImageScope. To avoid subjectivity in evaluation, the intensities and percentages of the staining were scored by two independent individuals in a semi-quantitative way as previously described and average was taken. BQ323636.1 expression level was scored according to the H-score system which takes into account the intensity of the staining and percentage of each intensity (Detre, Saclani Jotti et al. 1995). H score=(1×% of cells stained at intensity category 1)+(2×% of cells stained at intensity category 2)+(3×% of cells stained at intensity category 3). The cutoff was set as the median of the scores, which was 130.

Statistical analysis—Statistical analyses were conducted used SPSS (IBM, version 17). Results from MTT assays and mouse model were compared by students' t-test. The correlations between expression levels of splice variant BQ323636.1 and tamoxifen responsiveness of the patients were analyzed by Chi-square tests. The expression levels of BQ323636.1 were compared between different groups using Mann-Whiney U Rank test. Survival analyses were done by Kaplan-Meier estimates and Cox regression model. P values of less than 0.05 were considered statistically significant.

Example 1

Generation of Monoclonal Antibody Specific to BQ323636.1

The present invention involves the generation of a mouse monoclonal antibody whose epitope (QRTWRSRCASWP) (SEQ ID NO: 2) mapped to the last 11 amino acids of the BQ323636.1 protein (FIG. 1A), which is the sequence which distinguishes BQ323636.1 from its wild-type NCOR2/SMRT. The detailed protocol is described below.

Immunogen: Peptide 3781.1 Biosyntan GmbH QRTWRSRCASWP-OH Peptide-BSA-Conjugate (BSA: Fraction V, Pierce; Cross-Linker: Sulfo-MBS, Pierce)

Host: 8-week-old female BALB/c mice

Immunization Procedures:

| Immunisation (Day) | Injection | Doses (μg/mouse) | Adjuvant |
|---|---|---|---|
| 9 | Priming (i.p.) | 109 | TiterMax Gold Adjuvant |
| 14 | Boost 1 (i.p.) | 109 | Complete Freund's Adjuvant |

-continued

| Immunisation (Day) | Injection | Doses (μg/mouse) | Adjuvant |
|---|---|---|---|
| 21 | Boost 2 (i.p.) | 54 | Incomplete Freund's Adjuvant |
| 28 | Boost 3 (i.p.) | 54 | Incomplete Freund's Adjuvant |
| 35 | Boost 4 (i.p.) | 54 | PBS |
| 38 | Fusion | | Mouse 42 |

The presence of the desired antibody was detected in the sera of the recipients prior to the final booster dose using the enzyme-linked immunosorbent assay (ELISA) with the uncoupled Peptide 3781 as immobilized antigen. For fusion experiment mouse 42 was used.

Date of fusion: Apr. 10, 2013 Fusion number: 577

Parent cell fusion line: SP2/0 (non-secreting mouse myeloma)

Fusion method: Two days before fusion mouse (Balb/c) peritoneal macrophages for use as feeder cells were prepared and seeded into the wells of four 96-well cell culture plates. For fusion procedures, $6\times10^7$ spleen cells from the immunised mouse and $2\times10^7$ cells from mouse myeloma cell line SP2/0 were incubated with 1.2 ml of polyethylene glycol 1450 (50% in 10% DMSO; Sigma) for 30 sec. at 37° C. After washing, the cells were seeded in the four 96-well cell culture plates. Hybrid clones were selected by growing in HAT medium [RPMI 1640 culture medium (Biochrom) supplemented with 20% fetal calf serum (PAN) and HAT-Supplement (50×; PAN)]. After two weeks the HAT medium was replaced with HT Medium for three passages followed by returning to the normal cell culture medium.

Screening/Cloning/Recloning: The cell culture supernatants were primary screened for antigen specific IgG antibodies two weeks after fusion. The presence of antigen specific antibodies in the culture supernatants was measured by its binding to the uncoupled Peptide 3781 attached directly to the wells of 96-well microtiter plates (100 ng/well). The antibody binding was quantified by adding the relevant anti-species immunoglobulin to which an enzyme is bound, followed by a chromogenic substrate to that enzyme. Fresh culture medium and a dilution of the polyclonal mouse antiserum were used as negative or as positive controls. 12 specific antibody producing hybridoma colonies were found to be high positive. The selected 12 cell populations were transferred into 24-well plates for cell propagation and were then tested again. 4 cell populations with the highest antibodies titres were selected for cloning and re-cloning using the limiting-dilution technique. 4 cell lines producing specific monoclonal antibodies were characterized and frozen. For the isotype characterization the Mouse Monoclonal Antibody Isotyping Kit (Roche) was used.

Cell culture medium: RPMI 1640 Medium [(1×), w 2.0 g/1 NaHCO3, w stable Glutamine (Biochrom AG; Catalog No.: FG 1415)] with 20% FCS (PAN Biotech GmbH; Cat.-No.: 1302-P283004; Lot No.: P283004; Origin: Australia); Gentamicin (PAA Laboratories GmbH; Best.-Nr. P11-004; 50 μg/ml)

Optimal growth: At a temperature of 37° C. and 5% CO2

Storage of cells/Freezing: Approximately $3\times10^6$ cells in 7500 fresh cell culture medium were pipette into a cryotube. 750 μl of freezing medium (80% FCS and 20% DMSO (PAN)) were added. Using a Nalgene Cryo Freezing Container the cryotubes were placed in a −80° C. freezer immediately and transferred to liquid N2 within 24 hours for long-term storage.

Storage of cells/Thawing: The cryotubes were quickly thawed as possible in a 37° C. water bath. The cells were diluted with 10 ml cold medium and centrifuged at 1000 rpm for 10 min. Then the pellets were resuspended in cell culture medium and transferred into 25 ml cell culture flasks.

Test for mycoplasma: The cell culture supernatants were tested for mycoplasma using an ELISA Kit (Mycoplasma detection Kit; Roche Diagnostics GmbH)

Example 2

Reactivities of the Secreted Antibodies of the 4 Final Clones: ELISA

The cell culture supernatants were incubated with a solid phase to which the uncoupled Peptide 3781 has been bound by direct adsorption. During the assay any specific antibody will itself become bound to the antigen on the solid phase, and then in a second incubation is detected with a labelled anti-species antibody.

Coating: 100 ng/well (well=50 μl) of Peptide 3781 (diluted in PBS) overnight at 4° C.; wash plate twice with wash buffer (PBS/0.05% Tween20). Blocking: 100 μl/well blocking solution (PBS/0.05% Tween20/10% NCS) for 1 h at RT;

Wash plates twice with wash buffer. Incubation: 50 μl/well of the cell culture supernatants serial diluted in incubation buffer (PBS/0.05%; Tween20/10% NCS) for 2 h at RT; wash plates three times with wash buffer. Conjugate: 50 μl/well HRP-Rabbit anti Mouse IgG; (Fc specific; Pierce; diluted in incubation buffer) for 1 h at RT; wash plates three times with wash buffer. Substrate: 50 μl/well enzyme substrate (OPD in citrate-hydrogenphosphate buffer) for 15 min at RT. Stopping: 50 μl/well stopping solution. Measure: Measure absorbance at 490 nm Substrate: 3.7 mM o-Phenylendiamine in Citrate/Hydrogenphosphate buffer, 0.012% H2O2 Citrate/Hydrogenphosphate buffer: 35 mM Citric acid Monohydrate, 85 mM Na2HPO4×2H2O, pH 5.0 Stopping solution: 4N Schwefelsäure. Wash buffer: PBS/0.05% Tween20.

Four clones (C1, D12, G4, H8) with highest titer of antigen specific antibody production were selected and ELISA was applied to assess the antigen-antibody specific binding (FIG. 1B).

Example 3

Testing of Anti-BQ323636.1 Antibody in Commonly Used Biomedical Research Methods The four clones of the anti-BQ323636.1 were tested in the application of western blot (FIG. 2A), immuno-precipitation (FIG. 2B), immunofluorescence staining (FIG. 2C) and immunohistochemistry staining (FIG. 2D). In western blot, this BQ323636.1 detects a specific band at molecular weight of slightly below 50 kDa (predicted molecular weight is 42.65 kDa, antibody dilution 1:1000). Immuno-precipitation by clone G4 and D12 showed enrichment of the protein at molecular weight slightly below 50 kDa. Immunofluorescence staining (antibody dilution 1:50) showed that BQ323636.1 was expressed in both cytoplasm and nucleus of the cell, consistent with immunohistochemistry staining using breast cancer patients' samples (antibody dilution 1:50).

Example 4

Figure 3:
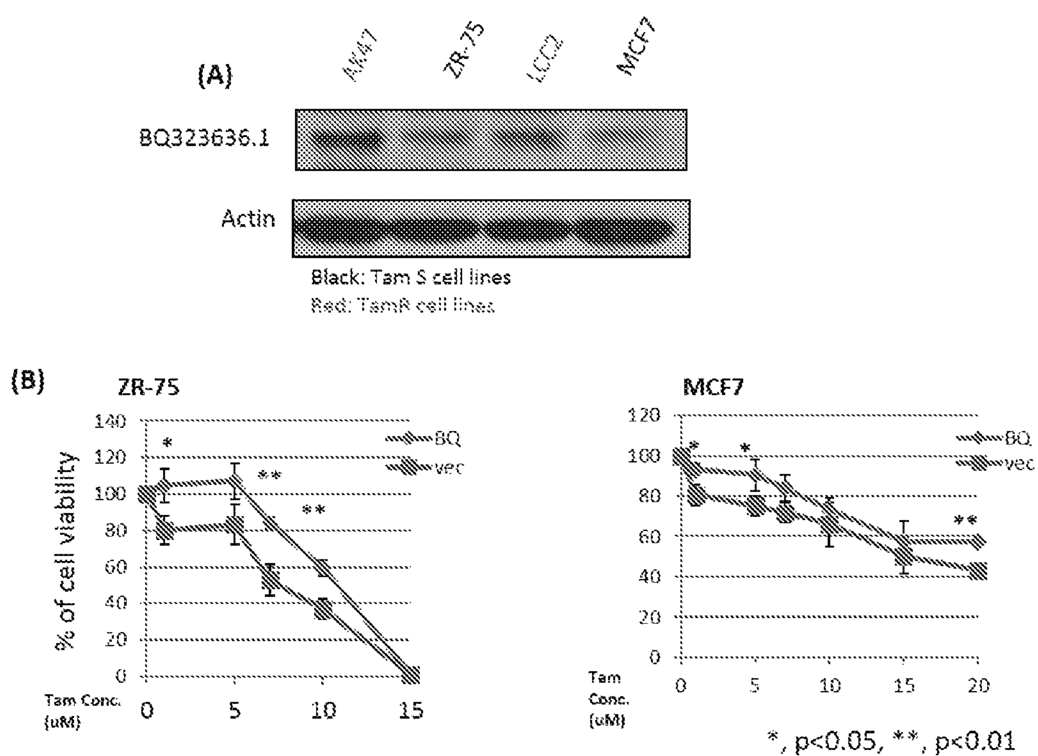
FIG. 3 indicates that (A) BQ323636.1 was expressed at higher level in tamoxifen resistant cell lines AK47 and LCC2 and (B) ectopic over-expression of BQ323636.1 induces tamoxifen resistance.

BQ323636.1 Overexpression Conferred Tamoxifen Resistance Both In Vitro and In Vivo Western blot using anti-BQ323636.1 antibody showed that, at protein level, BQ323636.1 expressed at higher level in the derived tamoxifen resistant cell lines LCC2 and AK47 compared to their parental tamoxifen sensitive cell lines MCF7 and ZR75, respectively (FIG. 3A). Using lentiviral-based system, we generated cell lines that were stably overexpressing BQ323636.1 (ZR75-BQ323636.1 and MCF7-BQ323636.1) (FIG. 10) and cell lines transfected with empty vector were used as the control (ZR75-vector and MCF7-vector). MTT assays showed that BQ323636.1 overexpression induced the tamoxifen resistance, as shown in FIG. 3B.

We further validated the effect of BQ323636.1 overexpression in conferring tamoxifen resistance using a nude mouse model. The cell lines mixed with Matrigel (BD Biosciences) at the ratio of 1:1 were inoculated into the abdominal mammary fat pad of the 5 to 6 week old female nude mice. When the tumors were palpable, the mice were randomized into treatment and control groups where treatment groups received daily subcutaneous injection of tamoxifen (Sigma) dissolved in peanut oil (Sigma) and the control groups received equivalent amount of solvent only. Tumor sizes were measured by caliper and tumor volume was calculated as (length*width*width)/2. Tumor growth rate was expressed as the % of tumor volume change calculated as the tumor volume measured at the indicated time point normalized against the tumor volume at day 0*100%. As shown in FIG. 4A, the control cell lines, ZR75-vector and MCF7-vector, which are originally tamoxifen sensitive, responded well to tamxoifen treatment, as marked by the significantly reduced tumor growth when compared with the control group which had received solvent treatment only. In contrast, BQ323636.1 over-expressing cell lines, both ZR75-BQ32363.61 and MCF7-BQ323636.1 (FIG. 4B), were resistant to the tamoxifen treatment, as there was no change of tumor growth compared between treatment and control group. Both the in vitro and in vivo results confirmed that BQ323636.1 overexpression conferred tamoxifen resistance, which provide solid experimental evidence for the use of BQ323636.1 as a predictive marker for tamoxifen resistance.

Example 5

Use of Monoclonal Antibody Anti-BQ323636.1 in IHC for Prediction of Tamoxifen Resistance in Breast Cancer Patients As in vivo confirmation of the usefulness of BQ323636.1 as a predictive marker for tamoxifen resistance in human tissue samples, the efficacy of using monoclonal antibody specific for BQ323636.1 was assessed by IHC staining on tissue microarray on a total of 355 patients who had received tamoxifen treatment. These tamoxifen treated patients were from Hong Kong, (93 cases) and from the United Kingdom (262 cases). Both cohorts of patients when analyzed separately, each gave statistically significant results. Hence the pooled results are presented. Tamoxifen resistance was defined as patients who received tamoxifen treatment and subsequently developed disease relapse or metastasis.

Nuclear BQ323636.1 overexpression was significantly associated with tamoxifen resistance by Chi-square test ($p=3.90\times10^{-6}$, FIG. 5A) and BQ32363.1 nuclear expression was significantly higher in patients who were later found to be tamoxifen resistant (Mann-Whitney U Rank test, $p=4.02\times10^{-6}$, FIG. 5B). Nuclear BQ323636.1 overexpression was also significantly associated with disease relapse (Chi-square test, $p=3.47\times10^{-4}$, FIG. 6A) and nuclear BQ323636.1 was significantly higher in patients who later developed disease relapse (Mann-Whitney U Rank test, $p=3.54\times10^{-4}$, FIG. 6B). Moreover, nuclear BQ323636.1 overexpression was significantly correlated with cancer metastasis (Chi-square test, $p=1.72\times10^{-6}$, FIG. 7A) and nuclear BQ323636.1 was significantly higher in patients who later developed metastasis (Mann-Whitney U Rank test, $p=1.78\times10^{-6}$, FIG. 7B).

Consistent with its role in predicting tamoxifen resistance, nuclear BQ323636.1 overexpression was significantly associated with poorer survival by Kaplan-Meier estimate (Log-rank test, $p=6.28\times10^{-5}$ and $p=1.31\times10^{-4}$ for overall survival and disease-specific survival, respectively, FIG. 8). By cox regression univariate analysis (FIG. 9), it was also found that nuclear BQ323636.1 overexpression was significantly associated with poorer overall survival (risk ratio=1.842, p=0.000) as well as with poorer disease-specific survival (risk ratio=2.10, p=0.000). The significance was maintained on multivariate analysis with the association with poorer overall survival (risk ratio=2.41, p=0.000) as well as with poorer disease-specific survival (risk ratio=3.20, p=0.000).

Example 6

Sequencing of $V_H$ and $V_L$ Chains of the Monoclonal Antibody mRNA was extracted from the hybridoma cell pellets. Total RNA was extracted from the pellets using Fusion Antibodies Ltd in-house RNA extraction protocol.

Figure 11:
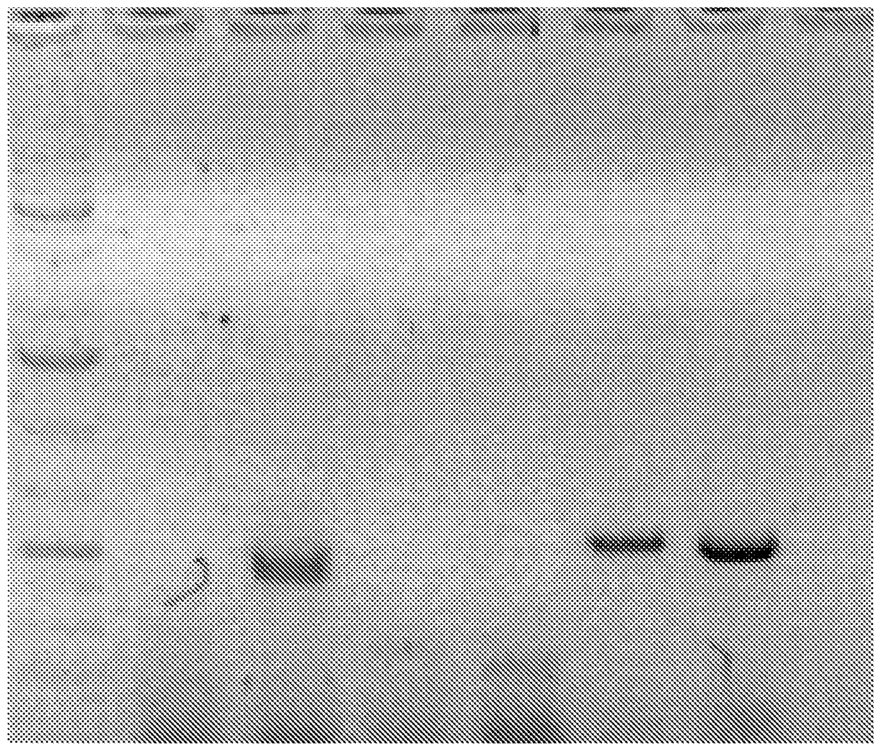
FIG. 11 shows PCR results several combinations of Ig variable domain primers.

RT-PCR: cDNA was created from the RNA by reverse-transcription with an oligo(dT) primer. PCR reactions are set up using variable domain primers to amplify both the $V_H$ and $V_L$ regions of the monoclonal antibody DNA giving the bands shown in FIG. 11. The $V_H$ and $V_L$ products were cloned into the Invitrogen sequencing vector pCR2.1 and transformed into TOP10 cells and screened by PCR for positive transformants. Selected colonies were picked and analyzed by DNA sequencing on an ABI3130xl Genetic Analyzer. Amino acid sequence alignments are shown for the heavy chain in FIG. 12 and the light chain in FIG. 13. The $V_H$ Consensus Amino Acid Sequence:

(SEQ ID NO: 3)

MYLGLSCVFIVFLLKGVQSEVKLEESGGGLVQPGGSMKLSCVASGFTFSNY

W(hCDR1)MNWVRQSPEKGLEWVAEIRLRSSYYAT(hCDR2)HYAESVKGR

FTISRDDSKSSVYLQMNNLRAEDTGIYYCTMITTGYFDV(hCDR3)WGAGT

TVTVSSAKTTPPSVYPLA

The variable domain is highlighted in BOLD. The Complementarity Determining Regions (CDRs) are underlined as determined by the IMGT numbering system (Lefranc, M. P. et al., *Nucleic Acids Research,* 27, 209-212 (1999)).

Figure 14:
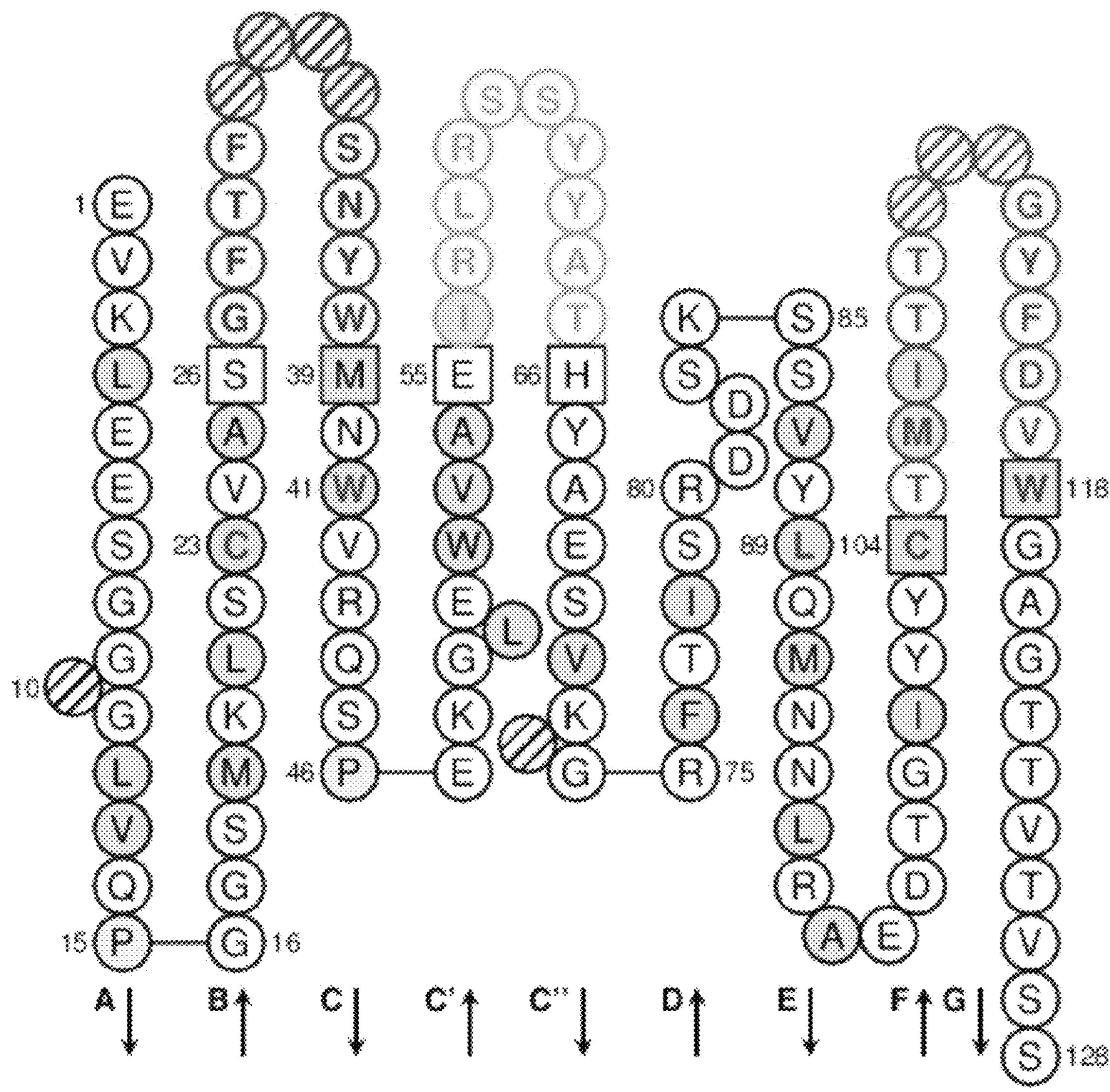
FIG. 14 shows a graphical representation of the variable domain and CDR loops for the heavy chain (SEQ ID NO: 3) of the monoclonal antibody of the present invention.

A graphical representation of the variable domain and the CDR loops for the heavy chain is shown in FIG. 14.

The amino acid sequences aligned in FIG. 12 include VH2.1 (SEQ ID NO: 32), VH2.2 (SEQ ID NO: 34), VH2.3 (SEQ ID NO: 35), VH2.5 (SEQ ID NO: 33), and VH2.6 (SEQ ID NO: 36), having corresponding nucleic acid sequences of SEQ ID NO: 9, SEQ ID NO: 10, SEQ ID NO: 11, SEQ ID NO: 12, and SEQ ID NO: 13, respectively.

$V_L$ Consensus Amino Acid Sequence:

(SEQ ID NO; 44)

MKLPVRLLVLMFWIPASSSDVVMTQTPLSLPVSLGDQASISCRSSQSLHI

SNGNTY(1CDR1)LHWYLQKPGQSPKLLIYKVS(1CDR2)NRFSGVPDRF

SGSGSGTDFTLKISRVEAEDLGVYFCSQITHIPRT(1CDR3)FGGGTKLE

IKRADAAPTVSIFPPSSEQLTSGGASVVCFLNNFYPK

The variable domain is highlighted in BOLD. The Complementarity Determining Regions (CDRs) are underlined as determined by the IMGT numbering system (Lefranc, M. P. et al., *Nucleic Acids Research,* 27, 209-212 (1999)).

Figure 15:
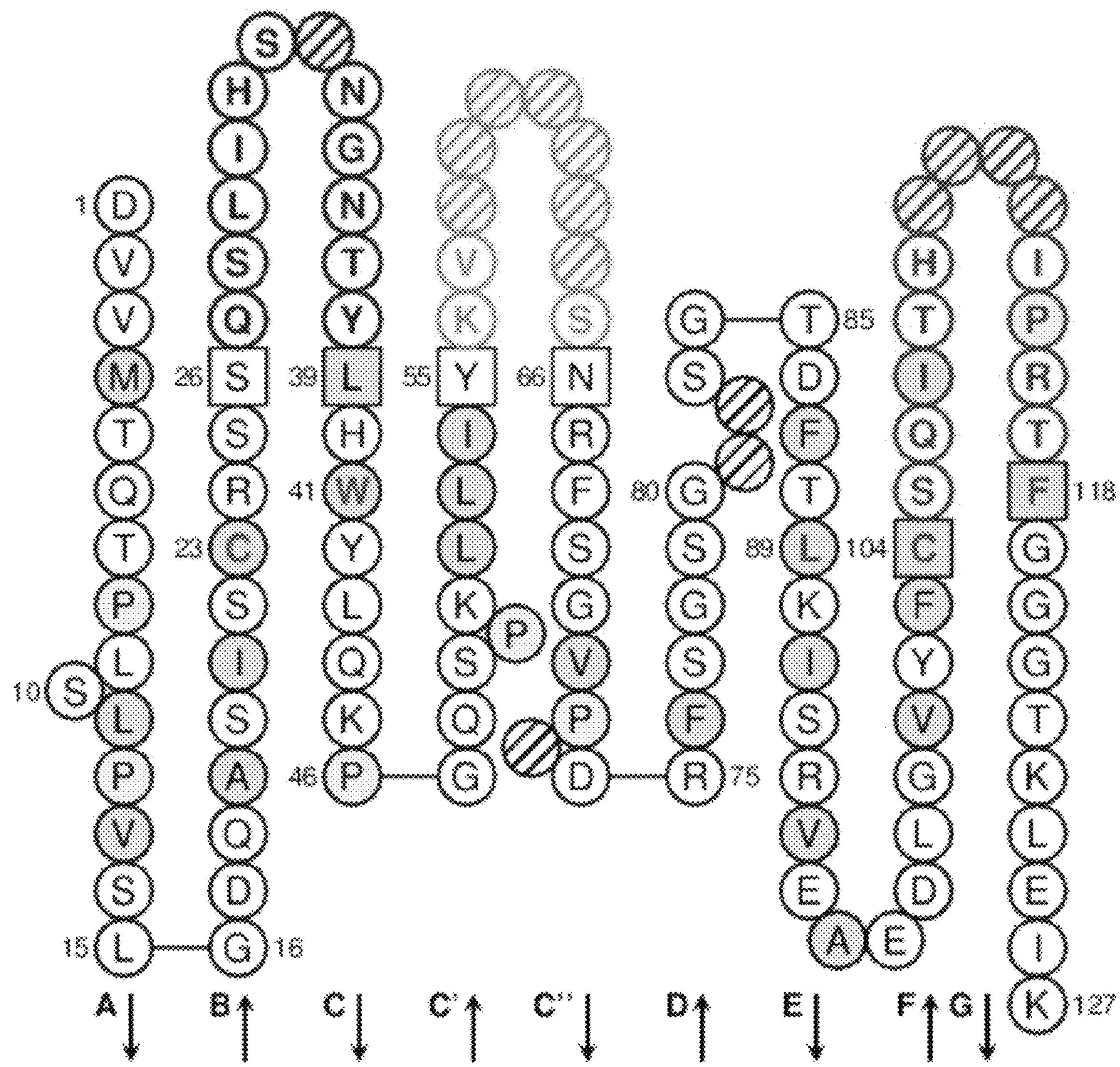
FIG. 15 shows a graphical representation of the variable domain and CDR loops for the light chain (SEQ ID NO: 44) of the monoclonal antibody of the present invention.

A graphical representation of the variable domain and the CDR loops for the heavy chain is shown in FIG. 15.

The amino acid sequences aligned in FIG. 13 include VK2.1 (SEQ ID NO: 42), VK2.2 (SEQ ID NO: 43), VK2(2).2 (SEQ ID NO: 38), VK2(2).3 (SEQ ID NO: 39), and VK2(2).5 (SEQ ID NO: 40), and VK2(2).6 (SEQ ID NO: 41), having corresponding nucleic acid sequences of SEQ ID NO: 20, SEQ ID NO: 21, SEQ ID NO: 22, SEQ ID NO: 23, SEQ ID NO: 24, and SEQ ID NO: 25, respectively.

DISCUSSION

The first front treatment for breast cancer patients is usually surgical resection. More than 70% of breast cancers express estrogen receptor (ER). ER positive patents are routinely treated with tamoxifen, a selective estrogen receptor modulator, as first-line adjuvant therapy to prevent cancer recurrence and reduce mortality rate. However, with prolonged tamoxifen treatment, almost half of patients will eventually develop resistance and present with disease recurrence or metastases. These patients will then need to be treated with chemotherapy and will generally do poorly.

Since about one-half of the breast patients with estrogen receptor—positive cancer fail on tamoxifen, identification of effective and reliable biomarkers that could be used to monitor tamoxifen efficacy and new targets to reverse tamoxifen resistance is of importance. In order to improve the disease outcome of breast cancer patients, establishment of more sensitive predictive biomarkers and novel therapeutic targets for patients who are refractory to tamoxifen treatment is needed. The present invention provides a monoclonal antibody specific for BQ323636.1 and the use of it in assays, such as immunohistochemistry (IHC), for prediction of tamoxifen resistance in breast cancer patients. BQ323636.1, a splice variant of NCOR2/SMRT, was identified to be associated with tamoxifen resistance and a mouse monoclonal antibody specific for this splice variant was generated to study the efficacy of using BQ323636.1 as a predictive marker for tamoxifen resistance. Using this antibody, it was found that overexpression of BQ323636.1 conferred resistance to tamoxifen both in vitro using cell lines and in vivo using nude mice model. Using this antibody in IHC on tissue microarrays (TMA) constructed from 355 cases of archived breast cancer patients' paraffin blocks successfully showed that BQ323636.1 overexpression could predict tamoxifen resistance ($p=3.90\times10^{-6}$) (tamoxifen resistance being defined as patients who received tamoxifen and later developed relapse or metastasis) and was associated with poor patients' survival ($p=6.28\times10^{-5}$ for overall survival, $p=1.31\times10^{-4}$ for disease specific survival).

REFERENCES

Cheng, X. and H. Y. Kao (2009). "G protein pathway suppressor 2 (GPS2) is a transcriptional corepressor important for estrogen receptor alpha-mediated transcriptional regulation." *J Biol Chem* 284(52): 36395-36404.

Coller, J. K., N. Krebsfaenger, K. Klein, K. Endrizzi, R. Wolbold, T. Lang, A. Nussler, P. Neuhaus, U. M. Zanger, M. Eichelbaum and T. E. Murdter (2002). "The influence of CYP2B6, CYP2C9 and CYP2D6 genotypes on the formation of the potent antioestrogen Z-4-hydroxy-tamoxifen in human liver." *Br J Clin Pharmacol* 54(2): 157-167.

de Souza, J. A. and O. I. Olopade (2011). "CYP2D6 genotyping and tamoxifen: an unfinished story in the quest for personalized medicine." *Semin Oncol* 38(2): 263-273.

Dehal, S. S. and D. Kupfer (1997). "CYP2D6 catalyzes tamoxifen 4-hydroxylation in human liver." *Cancer Res* 57(16): 3402-3406.

Detre, S., G Saclani Jotti and M. Dowsett (1995). "A "quickscore" method for immunohistochemical semi-quantitation: validation for oestrogen receptor in breast carcinomas." *J Clin Pathol* 48(9): 876-878.

Dezentje, V. O., H. J. Guchelaar, J. W. Nortier, C. J. van de Velde and H. Gelderblom (2009). "Clinical implications of CYP2D6 genotyping in tamoxifen treatment for breast cancer." *Clin Cancer Res* 15(1): 15-21.

Hoskins, J. M., L. A. Carey and H. L. McLeod (2009). "CYP2D6 and tamoxifen: DNA matters in breast cancer." *Nat Rev Cancer* 9(8): 576-586.

Ring, A. and M. Dowsett (2004). "Mechanisms of tamoxifen resistance." *Endocr Relat Cancer* 11(4): 643-658.

Sharma, D., N. K. Saxena, N. E. Davidson and P. M. Vertino (2006). "Restoration of tamoxifen sensitivity in estrogen receptor-negative breast cancer cells: tamoxifen-bound reactivated ER recruits distinctive corepressor complexes." *Cancer Res* 66(12): 6370-6378.

Wong, L. J., P. Dai, J. F. Lu, M. A. Lou, R. Clarke and V Nazarov (2006). "A1B1 gene amplification and the instability of polyQ encoding sequence in breast cancer cell lines." *BMC Cancer* 6: 111.

Zhang, L., C. Gong, S. L. Lau, N. Yang, O. G Wong, A. N. Cheung, J. W. Tsang, K. Y. Chan and U. S. Khoo (2013). "SpliceArray profiling of breast cancer reveals a novel variant of NCOR2/SMRT that is associated with tamoxifen resistance and control of ERalpha transcriptional activity." *Cancer Res* 73(1): 246-255.

Zhang, X. M., Q. Chang, L. Zeng, J. Gu, S. Brown and R. S. Basch (2006). "TBLR1 regulates the expression of nuclear hormone receptor co-repressors." *BMC Cell Biol* 7: 31.

What is claimed is:

1. An antibody or antibody fragment comprising a heavy chain comprising CDR1, CDR2, and CDR3 sequences of GFTFSNYW (SEQ ID NO: 27), IRLRSSYYAT (SEQ ID NO: 28), and TMITTGYFDV (SEQ ID NO: 29), respectively; and a light chain comprising CDR1, CDR2, and CDR3 sequences of QSLIHSNGNTY (SEQ ID NO: 30), KVS, and SQITHIPRT (SEQ ID NO: 31), respectively.

2. The antibody or antibody fragment of claim 1 comprising a $V_H$ amino acid sequence of SEQ ID NO: 3 and a $V_L$ amino acid sequence of SEQ ID NO: 44.

3. The antibody or antibody fragment of claim 1, wherein the antibody is a chimeric or humanized antibody.

4. The antibody fragment of claim 1, wherein the antibody fragment is selected from Fab, Fab', Fab'-SH, F (ab') 2, Fv, diabodies, single-chain antibody fragment, or a multispecific antibody comprising multiple different antibody fragments.

5. The antibody or antibody fragment of claim 1, wherein said antibody or antibody fragment is conjugated or covalently bound to a detectable moiety.

6. An antibody obtained by chimerizing or humanizing an antibody of claim 1.

7. The antibody or antibody fragment of claim 1, wherein the antibody or antibody fragment is a monoclonal antibody.

8. A kit comprising the antibody or antibody fragment of claim 1, the kit optionally further comprising a labeled secondary antibody that specifically recognizes the antibody or antibody fragment of claim 1.

9. A hybridoma or recombinant host cell producing the antibody or antibody fragment of claim 1.

10. A method of determining tamoxifen resistance in a subject with cancer, comprising:

(a) obtaining a tumor sample from the subject;

(b) determining in the sample a level of expression for a splice variant of NCOR2, wherein the splice variant is characterized by an exon 11 deletion during mRNA splicing resulting in an early translation stop codon and truncated protein product, wherein said determining the expression level comprises using the antibody or antibody fragment of claim 1; and (c) comparing the expression level in (b) to a level of expression in a normal control, wherein overexpression of the splice variant of NCOR2, with respect to the control, indicates that the cancer is tamoxifen resistant.

11. The method of claim 10, wherein the subject is a human.

12. The method of claim 10, wherein the cancer is breast cancer.

13. The method according to claim 10, wherein the splice variant of NCOR2 is contacted with the antibody or antibody fragment that specifically recognizes the splice variant of NCOR2 in an immunoassay selected from the group consisting of radioimmunoassay, western blot assay, immunofluorescent assay, enzyme immunoassay, immunoprecipitation, chemiluminescent assay, immunohistochemical assay, dot blot assay, and slot blot assay.

14. A method of determining whether a tamoxifen-treated subject is at risk of cancer relapse, or at risk for metastasis, comprising:

(a) obtaining a tumor sample from the tamoxifen-treated subject;

(b) determining in the sample a level of expression for a splice variant of NCOR2, wherein the splice variant is characterized by an exon 11 deletion during mRNA splicing resulting in an early translation stop codon and truncated protein wherein said determining the level of expression comprises using the antibody or antibody fragment of claim 1; and (c) comparing the expression level in (b) to a level of expression in a normal control, wherein overexpression of the splice variant of NCOR2, with respect to the control, indicates that the tamoxifen-treated subject is at risk of cancer relapse or is at risk for metastasis.

15. The method of claim 14, wherein the subject is a human.

16. The method of claim 15, wherein the cancer is breast cancer.

17. A hybridoma deposited with the Leibniz Institute DSMZ-German Collection of Microorganisms and Cell Cultures under the deposit no. 577/D12-DSM ACC3272.

* * * * *

SEQUENCE LISTING

```
<160> NUMBER OF SEQ ID NOS: 44

<210> SEQ ID NO 1
<211> LENGTH: 362
```

```
<212> TYPE: PRT
<213> ORGANISM: Mus musculus

<400> SEQUENCE: 1

Met Ser Gly Ser Thr Gln Pro Val Ala Gln Thr Trp Arg Ala Thr Glu
1               5                   10                  15

Pro Arg Tyr Pro Pro His Ser Leu Ser Tyr Pro Val Gln Ile Ala Arg
            20                  25                  30

Thr His Thr Asp Val Gly Leu Leu Glu Tyr Gln His His Ser Arg Asp
        35                  40                  45

Tyr Ala Ser His Leu Ser Pro Gly Ser Ile Ile Gln Pro Gln Arg Arg
    50                  55                  60

Arg Pro Ser Leu Leu Ser Glu Phe Gln Pro Gly Asn Glu Arg Ser Gln
65                  70                  75                  80

Glu Leu His Leu Arg Pro Glu Ser His Ser Tyr Leu Pro Glu Leu Gly
                85                  90                  95

Lys Ser Glu Met Glu Phe Ile Glu Ser Lys Arg Pro Arg Leu Glu Leu
            100                 105                 110

Leu Pro Asp Pro Leu Leu Arg Pro Ser Pro Leu Leu Ala Thr Gly Gln
        115                 120                 125

Pro Ala Gly Ser Glu Asp Leu Thr Lys Asp Arg Ser Leu Thr Gly Lys
    130                 135                 140

Leu Glu Pro Val Ser Pro Pro Ser Pro Pro His Thr Asp Pro Glu Leu
145                 150                 155                 160

Glu Leu Val Pro Pro Arg Leu Ser Lys Glu Glu Leu Ile Gln Asn Met
                165                 170                 175

Asp Arg Val Asp Arg Glu Ile Thr Met Val Glu Gln Gln Ile Ser Lys
            180                 185                 190

Leu Lys Lys Lys Gln Gln Gln Leu Glu Glu Glu Ala Ala Lys Pro Pro
        195                 200                 205

Glu Pro Glu Lys Pro Val Ser Pro Pro Pro Ile Glu Ser Lys His Arg
    210                 215                 220

Ser Leu Val Gln Ile Ile Tyr Asp Glu Asn Arg Lys Lys Ala Glu Ala
225                 230                 235                 240

Ala His Arg Ile Leu Glu Gly Leu Gly Pro Gln Val Glu Leu Pro Leu
                245                 250                 255

Tyr Asn Gln Pro Ser Asp Thr Arg Gln Tyr His Glu Asn Ile Lys Ile
            260                 265                 270

Asn Gln Ala Met Arg Lys Lys Leu Ile Leu Tyr Phe Lys Arg Arg Asn
        275                 280                 285

His Ala Arg Lys Gln Trp Glu Gln Lys Phe Cys Gln Arg Tyr Asp Gln
    290                 295                 300

Leu Met Glu Ala Trp Glu Lys Lys Val Glu Arg Ile Glu Asn Asn Pro
305                 310                 315                 320

Arg Arg Arg Ala Lys Glu Ser Lys Val Arg Glu Tyr Tyr Glu Lys Gln
                325                 330                 335

Phe Pro Glu Ile Arg Lys Gln Arg Glu Leu Gln Glu Arg Met Gln Arg
            340                 345                 350

Thr Trp Arg Ser Arg Cys Ala Ser Trp Pro
        355                 360


<210> SEQ ID NO 2
<211> LENGTH: 12
<212> TYPE: PRT
<213> ORGANISM: Mus musculus
```

```
<400> SEQUENCE: 2

Gln Arg Thr Trp Arg Ser Arg Cys Ala Ser Trp Pro
1               5                   10


<210> SEQ ID NO 3
<211> LENGTH: 150
<212> TYPE: PRT
<213> ORGANISM: Mus musculus

<400> SEQUENCE: 3

Met Tyr Leu Gly Leu Ser Cys Val Phe Ile Val Phe Leu Leu Lys Gly
1               5                   10                  15

Val Gln Ser Glu Val Lys Leu Glu Glu Ser Gly Gly Gly Leu Val Gln
            20                  25                  30

Pro Gly Gly Ser Met Lys Leu Ser Cys Val Ala Ser Gly Phe Thr Phe
        35                  40                  45

Ser Asn Tyr Trp Met Asn Trp Val Arg Gln Ser Pro Glu Lys Gly Leu
    50                  55                  60

Glu Trp Val Ala Glu Ile Arg Leu Arg Ser Ser Tyr Tyr Ala Thr His
65                  70                  75                  80

Tyr Ala Glu Ser Val Lys Gly Arg Phe Thr Ile Ser Arg Asp Asp Ser
                85                  90                  95

Lys Ser Ser Val Tyr Leu Gln Met Asn Asn Leu Arg Ala Glu Asp Thr
            100                 105                 110

Gly Ile Tyr Tyr Cys Thr Met Ile Thr Thr Gly Tyr Phe Asp Val Trp
        115                 120                 125

Gly Ala Gly Thr Thr Val Thr Val Ser Ser Ala Lys Thr Thr Pro Pro
    130                 135                 140

Ser Val Tyr Pro Leu Ala
145                 150


<210> SEQ ID NO 4
<211> LENGTH: 150
<212> TYPE: PRT
<213> ORGANISM: Mus musculus

<400> SEQUENCE: 4

Met Tyr Leu Gly Leu Ser Cys Val Phe Ile Val Phe Leu Leu Lys Gly
1               5                   10                  15

Val Gln Ser Glu Val Lys Leu Glu Glu Ser Gly Gly Gly Leu Val Gln
            20                  25                  30

Pro Gly Gly Ser Met Lys Leu Ser Cys Val Ala Ser Gly Phe Thr Phe
        35                  40                  45

Ser Asn Tyr Trp Met Asn Trp Val Arg Gln Ser Pro Glu Lys Gly Leu
    50                  55                  60

Glu Trp Val Ala Glu Ile Arg Leu Arg Ser Ser Tyr Tyr Ala Thr His
65                  70                  75                  80

Tyr Ala Glu Ser Val Lys Gly Arg Phe Thr Ile Ser Arg Asp Asp Ser
                85                  90                  95

Lys Ser Ser Val Tyr Leu Gln Met Asn Asn Leu Arg Ala Glu Asp Thr
            100                 105                 110

Gly Ile Tyr Tyr Cys Thr Met Ile Thr Thr Gly Tyr Phe Asp Val Trp
        115                 120                 125

Gly Ala Gly Thr Thr Val Thr Val Ser Ser Ala Lys Thr Thr Pro Pro
    130                 135                 140
```

```
Ser Val Tyr Pro Leu Val
145                 150


<210> SEQ ID NO 5
<211> LENGTH: 150
<212> TYPE: PRT
<213> ORGANISM: Mus musculus

<400> SEQUENCE: 5

Met Tyr Leu Gly Leu Ser Cys Val Phe Ile Val Phe Leu Leu Lys Gly
1               5                   10                  15

Val Gln Ser Glu Val Lys Leu Glu Glu Ser Gly Gly Gly Leu Val Gln
            20                  25                  30

Pro Gly Gly Ser Met Lys Leu Ser Cys Val Ala Ser Gly Phe Thr Phe
        35                  40                  45

Ser Asn Tyr Trp Met Asn Trp Val Arg Gln Ser Pro Glu Lys Gly Leu
    50                  55                  60

Glu Trp Val Ala Glu Ile Arg Leu Arg Ser Ser Tyr Tyr Ala Thr His
65                  70                  75                  80

Tyr Ala Glu Ser Val Lys Gly Arg Phe Thr Ile Ser Arg Asp Asp Ser
                85                  90                  95

Lys Ser Ser Val Tyr Leu Gln Met Asn Asn Leu Arg Ala Glu Asp Thr
            100                 105                 110

Gly Ile Tyr Tyr Cys Thr Met Ile Thr Thr Gly Tyr Phe Asp Val Trp
        115                 120                 125

Gly Ala Gly Thr Thr Val Thr Val Ser Ser Ala Lys Thr Thr Pro Pro
    130                 135                 140

Ser Val Tyr Pro Leu Val
145                 150


<210> SEQ ID NO 6
<211> LENGTH: 150
<212> TYPE: PRT
<213> ORGANISM: Mus musculus

<400> SEQUENCE: 6

Met Tyr Leu Gly Leu Ser Cys Val Phe Ile Val Phe Leu Leu Lys Gly
1               5                   10                  15

Val Gln Ser Glu Val Lys Leu Glu Glu Ser Gly Gly Gly Leu Val Gln
            20                  25                  30

Pro Gly Gly Ser Met Lys Leu Ser Cys Val Ala Ser Gly Phe Thr Phe
        35                  40                  45

Ser Asn Tyr Trp Met Asn Trp Val Arg Gln Ser Pro Glu Lys Gly Leu
    50                  55                  60

Glu Trp Val Ala Glu Ile Arg Leu Arg Ser Ser Tyr Tyr Ala Thr His
65                  70                  75                  80

Tyr Ala Glu Ser Val Lys Gly Arg Phe Thr Ile Ser Arg Asp Asp Ser
                85                  90                  95

Lys Ser Ser Val Tyr Leu Gln Met Asn Asn Leu Arg Ala Glu Asp Thr
            100                 105                 110

Gly Ile Tyr Tyr Cys Thr Met Ile Thr Thr Gly Tyr Phe Asp Val Trp
        115                 120                 125

Gly Ala Gly Thr Thr Val Thr Val Ser Ser Ala Lys Thr Thr Pro Pro
    130                 135                 140

Ser Val Tyr Pro Leu Ala
145                 150
```

<210> SEQ ID NO 7
<211> LENGTH: 150
<212> TYPE: PRT
<213> ORGANISM: Mus musculus

<400> SEQUENCE: 7

```
Met Tyr Leu Gly Leu Ser Cys Val Phe Ile Val Phe Leu Leu Lys Gly
1               5                   10                  15

Val Gln Ser Glu Val Lys Leu Glu Glu Ser Gly Gly Gly Leu Val Gln
            20                  25                  30

Pro Gly Gly Ser Met Lys Leu Ser Cys Val Ala Ser Gly Phe Thr Phe
        35                  40                  45

Ser Asn Tyr Trp Met Asn Trp Val Arg Gln Ser Pro Glu Lys Gly Leu
    50                  55                  60

Glu Trp Val Ala Glu Ile Arg Leu Arg Ser Ser Tyr Tyr Ala Thr His
65                  70                  75                  80

Tyr Ala Glu Ser Val Lys Gly Arg Phe Thr Ile Ser Arg Asp Asp Ser
                85                  90                  95

Lys Ser Ser Val Tyr Leu Gln Met Asn Asn Leu Arg Ala Glu Asp Thr
            100                 105                 110

Gly Ile Tyr Tyr Cys Thr Met Ile Thr Thr Gly Tyr Phe Asp Val Trp
        115                 120                 125

Gly Ala Gly Thr Thr Val Thr Val Ser Ser Ala Lys Thr Thr Pro Pro
    130                 135                 140

Ser Val Tyr Pro Leu Ala
145                 150
```

<210> SEQ ID NO 8
<211> LENGTH: 150
<212> TYPE: PRT
<213> ORGANISM: Mus musculus

<400> SEQUENCE: 8

```
Met Tyr Leu Gly Leu Ser Cys Val Phe Ile Val Phe Leu Leu Lys Gly
1               5                   10                  15

Val Gln Ser Glu Val Lys Leu Glu Glu Ser Gly Gly Gly Leu Val Gln
            20                  25                  30

Pro Gly Gly Ser Met Lys Leu Ser Cys Val Ala Ser Gly Phe Thr Phe
        35                  40                  45

Ser Asn Tyr Trp Met Asn Trp Val Arg Gln Ser Pro Glu Lys Gly Leu
    50                  55                  60

Glu Trp Val Ala Glu Ile Arg Leu Arg Ser Ser Tyr Tyr Ala Thr His
65                  70                  75                  80

Tyr Ala Glu Ser Val Lys Gly Arg Phe Thr Ile Ser Arg Asp Asp Ser
                85                  90                  95

Lys Ser Ser Val Tyr Leu Gln Met Asn Asn Leu Arg Ala Glu Asp Thr
            100                 105                 110

Gly Ile Tyr Tyr Cys Thr Met Ile Thr Thr Gly Tyr Phe Asp Val Trp
        115                 120                 125

Gly Ala Gly Thr Thr Val Thr Val Ser Ser Ala Lys Thr Thr Pro Pro
    130                 135                 140

Ser Val Tyr Pro Leu Ala
145                 150
```

<210> SEQ ID NO 9
<211> LENGTH: 450

<212> TYPE: DNA
<213> ORGANISM: Mus musculus

<400> SEQUENCE: 9

```
atgtacttgg gactgagctg tgtattcata gtttttctct taaaaggtgt ccagagtgaa     60

gtgaagcttg aggagtctgg aggaggcttg gtgcaacctg gaggatccat gaaactctcc    120

tgtgttgcct ctggattcac tttcagtaat tactggatga actgggtccg ccagtctcca    180

gagaaggggc ttgagtgggt tgctgaaatt agattgagat ctagttatta tgcaacacat    240

tatgcggagt ctgtgaaagg gaggttcacc atctcaagag atgattccaa aagtagtgtc    300

tacctgcaaa tgaacaactt aagagctgaa gacactggca tttattactg tactatgatt    360

acgacggggt acttcgatgt ctggggcgca gggaccacgg tcaccgtctc ctcagccaaa    420

acgacacccc catccgttta tcccttggtc                                     450
```

<210> SEQ ID NO 10
<211> LENGTH: 450
<212> TYPE: DNA
<213> ORGANISM: Mus musculus

<400> SEQUENCE: 10

```
atgtacttgg gactgagctg tgtattcata gtttttctct taaaaggtgt ccagagtgaa     60

gtgaagcttg aggagtctgg aggaggcttg gtgcaacctg gaggatccat gaaactctcc    120

tgtgttgcct ctggattcac tttcagtaat tactggatga actgggtccg ccagtctcca    180

gagaaggggc ttgagtgggt tgctgaaatt agattgagat ctagttatta tgcaacacat    240

tatgcggagt ctgtgaaagg gaggttcacc atctcaagag atgattccaa aagtagtgtc    300

tacctgcaaa tgaacaactt aagagctgaa gacactggca tttattactg tactatgatt    360

acgacggggt acttcgatgt ctggggcgca gggaccacgg tcaccgtctc ctcagccaaa    420

acgacacccc catctgtcta tccactggcc                                     450
```

<210> SEQ ID NO 11
<211> LENGTH: 450
<212> TYPE: DNA
<213> ORGANISM: Mus musculus

<400> SEQUENCE: 11

```
atgtacttgg gactgagctg tgtattcata gtttttctct taaaaggtgt ccagagtgaa     60

gtgaagcttg aggagtctgg aggaggcttg gtgcaacctg gaggatccat gaaactctcc    120

tgtgttgcct ctggattcac tttcagtaat tactggatga actgggtccg ccagtctcca    180

gagaaggggc ttgagtgggt tgctgaaatt agattgagat ctagttatta tgcaacacat    240

tatgcggagt ctgtgaaagg gaggttcacc atctcaagag atgattccaa aagtagtgtc    300

tacctgcaaa tgaacaactt aagagctgaa gacactggca tttattactg tactatgatt    360

acgacggggt acttcgatgt ctggggcgca gggaccacgg tcaccgtctc ctcagccaaa    420

acgacacccc catctgtcta tccactggcc                                     450
```

<210> SEQ ID NO 12
<211> LENGTH: 450
<212> TYPE: DNA
<213> ORGANISM: Mus musculus

<400> SEQUENCE: 12

```
atgtacttgg gactgagctg tgtattcata gtttttctct taaaaggtgt ccagagtgaa     60
```

```
gtgaagcttg aggagtctgg aggaggcttg gtgcaacctg gaggatccat gaaactctcc    120

tgtgttgcct ctggattcac tttcagtaat tactggatga actgggtccg ccagtctcca    180

gagaaggggc ttgagtgggt tgctgaaatt agattgagat ctagttatta tgcaacacat    240

tatgcggagt ctgtgaaagg gaggttcacc atctcaagag atgattccaa aagtagtgtc    300

tacctgcaaa tgaacaactt aagagctgaa gacactggca tttattactg tactatgatt    360

acgacggggt acttcgatgt ctggggcgca gggaccacgg tcaccgtctc ctcagccaaa    420

acgacacccc catccgttta tcccttggtc                                     450


<210> SEQ ID NO 13
<211> LENGTH: 450
<212> TYPE: DNA
<213> ORGANISM: Mus musculus

<400> SEQUENCE: 13

atgtacttgg gactgagctg tgtattcata gtttttctct taaaaggtgt ccagagtgaa     60

gtgaagcttg aggagtctgg aggaggcttg gtgcaacctg gaggatccat gaaactctcc    120

tgtgttgcct ctggattcac tttcagtaat tactggatga actgggtccg ccagtctcca    180

gagaaggggc ttgagtgggt tgctgaaatt agattgagat ctagttatta tgcaacacat    240

tatgcggagt ctgtgaaagg gaggttcacc atctcaagag atgattccaa aagtagtgtc    300

tacctgcaaa tgaacaactt aagagctgaa gacactggca tttattactg tactatgatt    360

acgacggggt acttcgatgt ctggggcgca gggaccacgg tcaccgtctc ctcagccaaa    420

acgacacccc catctgtcta tccactggcc                                     450


<210> SEQ ID NO 14
<211> LENGTH: 166
<212> TYPE: PRT
<213> ORGANISM: Mus musculus

<400> SEQUENCE: 14

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Ile His Ser Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ile Thr His Ile Pro Arg Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys
                165
```

<210> SEQ ID NO 15
<211> LENGTH: 166
<212> TYPE: PRT
<213> ORGANISM: Mus musculus

<400> SEQUENCE: 15

```
Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Ile His Ser Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ile Thr His Ile Pro Arg Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys
                165
```

<210> SEQ ID NO 16
<211> LENGTH: 166
<212> TYPE: PRT
<213> ORGANISM: Mus musculus

<400> SEQUENCE: 16

```
Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Ile His Ser Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ile Thr His Ile Pro Arg Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160
```

```
Asn Asn Phe Tyr Pro Lys
                165


<210> SEQ ID NO 17
<211> LENGTH: 166
<212> TYPE: PRT
<213> ORGANISM: Mus musculus

<400> SEQUENCE: 17

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Ile His Ser Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ile Thr His Ile Pro Arg Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys
                165


<210> SEQ ID NO 18
<211> LENGTH: 166
<212> TYPE: PRT
<213> ORGANISM: Mus musculus

<400> SEQUENCE: 18

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Ile His Ser Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ile Thr His Ile Pro Arg Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140
```

```
Ser Ser Glu Gln Leu Thr Ser Gly Gly Ala Ser Val Val Cys Phe Leu
145                 150                 155                 160

Asn Asn Phe Tyr Pro Arg
                165


<210> SEQ ID NO 19
<211> LENGTH: 166
<212> TYPE: PRT
<213> ORGANISM: Mus musculus

<400> SEQUENCE: 19

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Ile His Ser Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ile Thr His Ile Pro Arg Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Arg
                165


<210> SEQ ID NO 20
<211> LENGTH: 498
<212> TYPE: DNA
<213> ORGANISM: Mus musculus

<400> SEQUENCE: 20

atgaagttgc ctgttaggct gttggtgctg atgttctgga ttcctgcttc cagcagtgat      60

gttgtgatga cccaaactcc gctctccctg cctgtcagtc ttggagatca agcctccatc     120

tcttgcagat ctagtcagag ccttatacac agtaatggaa acacctattt gcattggtac     180

ctgcagaagc caggccagtc tccaaagctc ctgatctaca aagtttccaa ccgattttct     240

ggggtcccag acaggttcag tggcagtgga tcagggacag atttcacact caagatcagc     300

agagtggagg ctgaggatct gggagtttat ttctgctctc aaattacaca tattccgcgg     360

acgttcggtg gaggcaccaa gctggagatc aaacgggctg atgctgcacc aactgtatcc     420

atcttcccac catccagtga gcagttaaca tctggaggtg cctcagtcgt gtgcttcttg     480

aacaacttct accccaaa                                                   498


<210> SEQ ID NO 21
<211> LENGTH: 498
<212> TYPE: DNA
<213> ORGANISM: Mus musculus
```

<400> SEQUENCE: 21

```
atgaagttgc ctgttaggct gttggtgctg atgttctgga ttcctgcttc cagcagtgat     60
gttgtgatga cccaaactcc actctccctg cctgtcagtc ttggagatca agcctccatc    120
tcttgcagat ctagtcagag ccttatacac agtaatggaa acacctattt gcattggtac    180
ctgcagaagc caggccagtc tccaaagctc ctgatctaca aagtttccaa ccgattttct    240
ggggtcccag acaggttcag tggcagtgga tcagggacag atttcacact caagatcagc    300
agagtggagg ctgaggatct gggagtttat ttctgctctc aaattacaca tattccgcgg    360
acgttcggtg gaggcaccaa gctggagatc aaacgggctg atgctgcacc aactgtatcc    420
atcttcccac catccagtga gcagttaaca tctggaggtg cctcagtcgt gtgcttcttg    480
aacaacttct accccaaa                                                  498
```

<210> SEQ ID NO 22
<211> LENGTH: 498
<212> TYPE: DNA
<213> ORGANISM: Mus musculus

<400> SEQUENCE: 22

```
atgaagttgc ctgttaggct gttggtgctg atgttctgga ttcctgcttc cagcagtgat     60
gttgtgatga cccaaactcc actctccctg cctgtcagtc ttggagatca agcctccatc    120
tcttgcagat ctagtcagag ccttatacac agtaatggaa acacctattt gcattggtac    180
ctgcagaagc caggccagtc tccaaagctc ctgatctaca aagtttccaa ccgattttct    240
ggggtcccag acaggttcag tggcagtgga tcagggacag atttcacact caagatcagc    300
agagtggagg ctgaggatct gggagtttat ttctgctctc aaattacaca tattccgcgg    360
acgttcggtg gaggcaccaa gctggagatc aaacgggctg atgctgcacc aactgtatcc    420
atcttcccac catccagtga gcagttaaca tctggaggtg cctcagtcgt gtgcttcttg    480
aacaacttct accccaaa                                                  498
```

<210> SEQ ID NO 23
<211> LENGTH: 498
<212> TYPE: DNA
<213> ORGANISM: Mus musculus

<400> SEQUENCE: 23

```
atgaagttgc ctgttaggct gttggtgctg atgttctgga ttcctgcttc cagcagtgat     60
gttgtgatga cccaaactcc actctccctg cctgtcagtc ttggagatca agcctccatc    120
tcttgcagat ctagtcagag ccttatacac agtaatggaa acacctattt gcattggtac    180
ctgcagaagc caggccagtc tccaaagctc ctgatctaca aagtttccaa ccgattttct    240
ggggtcccag acaggttcag tggcagtgga tcagggacag atttcacact caagatcagc    300
agagtggagg ctgaggatct gggagtttat ttctgctctc aaattacaca tattccgcgg    360
acgttcggtg gaggcaccaa gctggagatc aaacgggctg atgctgcacc aactgtatcc    420
atcttcccac catccagtga gcagttaaca tctggaggtg cctcagtcgt gtgcttcttg    480
aacaacttct accccaaa                                                  498
```

<210> SEQ ID NO 24
<211> LENGTH: 498
<212> TYPE: DNA
<213> ORGANISM: Mus musculus

<400> SEQUENCE: 24

```
atgaagttgc ctgttaggct gttggtgctg atgttctgga ttcctgcttc cagcagtgat     60

gttgtgatga cccaaactcc actctccctg cctgtcagtc ttggagatca agcctccatc    120

tcttgcagat ctagtcagag ccttatacac agtaatggaa acacctattt gcattggtac    180

ctgcagaagc caggccagtc tccaaagctc ctgatctaca aagtttccaa ccgattttct    240

ggggtcccag acaggttcag tggcagtgga tcagggacag atttcacact caagatcagc    300

agagtggagg ctgaggatct gggagtttat ttctgctctc aaattacaca tattccgcgg    360

acgttcggtg gaggcaccaa gctggagatc aaacgggctg atgctgcacc aactgtatcc    420

atcttcccac catccagtga gcagttaaca tctggaggtg cctcagtcgt gtgcttcttg    480

aacaacttct accccaga                                                  498
```

```
<210> SEQ ID NO 25
<211> LENGTH: 498
<212> TYPE: DNA
<213> ORGANISM: Mus musculus

<400> SEQUENCE: 25

atgaagttgc ctgttaggct gttggtgctg atgttctgga ttcctgcttc cagcagtgat     60

gttgtgatga cccaaactcc actctccctg cctgtcagtc ttggagatca agcctccatc    120

tcttgcagat ctagtcagag ccttatacac agtaatggaa acacctattt gcattggtac    180

ctgcagaagc caggccagtc tccaaagctc ctgatctaca aagtttccaa ccgattttct    240

ggggtcccag acaggttcag tggcagtgga tcagggacag atttcacact caagatcagc    300

agagtggagg ctgaggatct gggagtttat ttctgctctc aaattacaca tattccgcgg    360

acgttcggtg gaggcaccaa gctggagatc aaacgggctg atgctgcacc aactgtatcc    420

atcttcccac catccagtga gcagttaaca tctggaggtg cctcagtcgt gtgcttcttg    480

aacaacttct accccaaa                                                  498
```

```
<210> SEQ ID NO 26
<211> LENGTH: 16
<212> TYPE: PRT
<213> ORGANISM: Mus musculus

<400> SEQUENCE: 26

Ser Gly Gly Ala Ser Val Val Cys Phe Leu Asn Asn Phe Tyr Pro Lys
1               5                   10                  15
```

```
<210> SEQ ID NO 27
<211> LENGTH: 8
<212> TYPE: PRT
<213> ORGANISM: Artificial Sequence
<220> FEATURE:
<223> OTHER INFORMATION: hCDR1

<400> SEQUENCE: 27

Gly Phe Thr Phe Ser Asn Tyr Trp
1               5
```

```
<210> SEQ ID NO 28
<211> LENGTH: 10
<212> TYPE: PRT
<213> ORGANISM: Artificial Sequence
<220> FEATURE:
<223> OTHER INFORMATION: hCDR2

<400> SEQUENCE: 28
```

```
Ile Arg Leu Arg Ser Ser Tyr Tyr Ala Thr
1               5                   10


<210> SEQ ID NO 29
<211> LENGTH: 10
<212> TYPE: PRT
<213> ORGANISM: Artificial Sequence
<220> FEATURE:
<223> OTHER INFORMATION: hCDR3

<400> SEQUENCE: 29

Thr Met Ile Thr Thr Gly Tyr Phe Asp Val
1               5                   10


<210> SEQ ID NO 30
<211> LENGTH: 11
<212> TYPE: PRT
<213> ORGANISM: Artificial Sequence
<220> FEATURE:
<223> OTHER INFORMATION: lCDR1

<400> SEQUENCE: 30

Gln Ser Leu Ile His Ser Asn Gly Asn Thr Tyr
1               5                   10


<210> SEQ ID NO 31
<211> LENGTH: 9
<212> TYPE: PRT
<213> ORGANISM: Artificial Sequence
<220> FEATURE:
<223> OTHER INFORMATION: lCDR3

<400> SEQUENCE: 31

Ser Gln Ile Thr His Ile Pro Arg Thr
1               5


<210> SEQ ID NO 32
<211> LENGTH: 150
<212> TYPE: PRT
<213> ORGANISM: Artificial Sequence
<220> FEATURE:
<223> OTHER INFORMATION: VH Amino Acid Sequence for VH2.1

<400> SEQUENCE: 32

Met Tyr Leu Gly Leu Ser Cys Val Phe Ile Val Phe Leu Leu Lys Gly
1               5                   10                  15

Val Gln Ser Glu Val Lys Leu Glu Glu Ser Gly Gly Gly Leu Val Gln
            20                  25                  30

Pro Gly Gly Ser Met Lys Leu Ser Cys Val Ala Ser Gly Phe Thr Phe
        35                  40                  45

Ser Asn Tyr Trp Met Asn Trp Val Arg Gln Ser Pro Glu Lys Gly Leu
    50                  55                  60

Glu Trp Val Ala Glu Ile Arg Leu Arg Ser Ser Tyr Tyr Ala Thr His
65                  70                  75                  80

Tyr Ala Glu Ser Val Lys Gly Arg Phe Thr Ile Ser Arg Asp Asp Ser
                85                  90                  95

Lys Ser Ser Val Tyr Leu Gln Met Asn Asn Leu Arg Ala Glu Asp Thr
            100                 105                 110

Gly Ile Tyr Tyr Cys Thr Met Ile Thr Thr Gly Tyr Phe Asp Val Trp
        115                 120                 125

Gly Ala Gly Thr Thr Val Thr Val Ser Ser Ala Lys Thr Thr Pro Pro
    130                 135                 140
```

```
Ser Val Tyr Pro Leu Val
145                 150


<210> SEQ ID NO 33
<211> LENGTH: 150
<212> TYPE: PRT
<213> ORGANISM: Artificial Sequence
<220> FEATURE:
<223> OTHER INFORMATION: VH Amino Acid Sequence for VH2.5

<400> SEQUENCE: 33

Met Tyr Leu Gly Leu Ser Cys Val Phe Ile Val Phe Leu Leu Lys Gly
1               5                   10                  15

Val Gln Ser Glu Val Lys Leu Glu Glu Ser Gly Gly Gly Leu Val Gln
            20                  25                  30

Pro Gly Gly Ser Met Lys Leu Ser Cys Val Ala Ser Gly Phe Thr Phe
        35                  40                  45

Ser Asn Tyr Trp Met Asn Trp Val Arg Gln Ser Pro Glu Lys Gly Leu
    50                  55                  60

Glu Trp Val Ala Glu Ile Arg Leu Arg Ser Ser Tyr Tyr Ala Thr His
65                  70                  75                  80

Tyr Ala Glu Ser Val Lys Gly Arg Phe Thr Ile Ser Arg Asp Asp Ser
                85                  90                  95

Lys Ser Ser Val Tyr Leu Gln Met Asn Asn Leu Arg Ala Glu Asp Thr
            100                 105                 110

Gly Ile Tyr Tyr Cys Thr Met Ile Thr Thr Gly Tyr Phe Asp Val Trp
        115                 120                 125

Gly Ala Gly Thr Thr Val Thr Val Ser Ser Ala Lys Thr Thr Pro Pro
    130                 135                 140

Ser Val Tyr Pro Leu Val
145                 150


<210> SEQ ID NO 34
<211> LENGTH: 150
<212> TYPE: PRT
<213> ORGANISM: Artificial Sequence
<220> FEATURE:
<223> OTHER INFORMATION: VH Amino Acid Sequence for VH2.2

<400> SEQUENCE: 34

Met Tyr Leu Gly Leu Ser Cys Val Phe Ile Val Phe Leu Leu Lys Gly
1               5                   10                  15

Val Gln Ser Glu Val Lys Leu Glu Glu Ser Gly Gly Gly Leu Val Gln
            20                  25                  30

Pro Gly Gly Ser Met Lys Leu Ser Cys Val Ala Ser Gly Phe Thr Phe
        35                  40                  45

Ser Asn Tyr Trp Met Asn Trp Val Arg Gln Ser Pro Glu Lys Gly Leu
    50                  55                  60

Glu Trp Val Ala Glu Ile Arg Leu Arg Ser Ser Tyr Tyr Ala Thr His
65                  70                  75                  80

Tyr Ala Glu Ser Val Lys Gly Arg Phe Thr Ile Ser Arg Asp Asp Ser
                85                  90                  95

Lys Ser Ser Val Tyr Leu Gln Met Asn Asn Leu Arg Ala Glu Asp Thr
            100                 105                 110

Gly Ile Tyr Tyr Cys Thr Met Ile Thr Thr Gly Tyr Phe Asp Val Trp
        115                 120                 125

Gly Ala Gly Thr Thr Val Thr Val Ser Ser Ala Lys Thr Thr Pro Pro
    130                 135                 140
```

```
Ser Val Tyr Pro Leu Ala
145                 150


<210> SEQ ID NO 35
<211> LENGTH: 150
<212> TYPE: PRT
<213> ORGANISM: Artificial Sequence
<220> FEATURE:
<223> OTHER INFORMATION: VH Amino Acid Sequence for VH2.3

<400> SEQUENCE: 35

Met Tyr Leu Gly Leu Ser Cys Val Phe Ile Val Phe Leu Leu Lys Gly
1               5                   10                  15

Val Gln Ser Glu Val Lys Leu Glu Glu Ser Gly Gly Gly Leu Val Gln
            20                  25                  30

Pro Gly Gly Ser Met Lys Leu Ser Cys Val Ala Ser Gly Phe Thr Phe
        35                  40                  45

Ser Asn Tyr Trp Met Asn Trp Val Arg Gln Ser Pro Glu Lys Gly Leu
    50                  55                  60

Glu Trp Val Ala Glu Ile Arg Leu Arg Ser Ser Tyr Tyr Ala Thr His
65                  70                  75                  80

Tyr Ala Glu Ser Val Lys Gly Arg Phe Thr Ile Ser Arg Asp Asp Ser
                85                  90                  95

Lys Ser Ser Val Tyr Leu Gln Met Asn Asn Leu Arg Ala Glu Asp Thr
            100                 105                 110

Gly Ile Tyr Tyr Cys Thr Met Ile Thr Thr Gly Tyr Phe Asp Val Trp
        115                 120                 125

Gly Ala Gly Thr Thr Val Thr Val Ser Ser Ala Lys Thr Thr Pro Pro
    130                 135                 140

Ser Val Tyr Pro Leu Ala
145                 150


<210> SEQ ID NO 36
<211> LENGTH: 150
<212> TYPE: PRT
<213> ORGANISM: Artificial Sequence
<220> FEATURE:
<223> OTHER INFORMATION: VH Amino Acid Sequence for VH2.6

<400> SEQUENCE: 36

Met Tyr Leu Gly Leu Ser Cys Val Phe Ile Val Phe Leu Leu Lys Gly
1               5                   10                  15

Val Gln Ser Glu Val Lys Leu Glu Glu Ser Gly Gly Gly Leu Val Gln
            20                  25                  30

Pro Gly Gly Ser Met Lys Leu Ser Cys Val Ala Ser Gly Phe Thr Phe
        35                  40                  45

Ser Asn Tyr Trp Met Asn Trp Val Arg Gln Ser Pro Glu Lys Gly Leu
    50                  55                  60

Glu Trp Val Ala Glu Ile Arg Leu Arg Ser Ser Tyr Tyr Ala Thr His
65                  70                  75                  80

Tyr Ala Glu Ser Val Lys Gly Arg Phe Thr Ile Ser Arg Asp Asp Ser
                85                  90                  95

Lys Ser Ser Val Tyr Leu Gln Met Asn Asn Leu Arg Ala Glu Asp Thr
            100                 105                 110

Gly Ile Tyr Tyr Cys Thr Met Ile Thr Thr Gly Tyr Phe Asp Val Trp
        115                 120                 125

Gly Ala Gly Thr Thr Val Thr Val Ser Ser Ala Lys Thr Thr Pro Pro
```

```
    130                 135                 140

Ser Val Tyr Pro Leu Ala
145                 150


<210> SEQ ID NO 37
<211> LENGTH: 150
<212> TYPE: PRT
<213> ORGANISM: Artificial Sequence
<220> FEATURE:
<223> OTHER INFORMATION: VH Amino Acid Sequence for Consensus

<400> SEQUENCE: 37

Met Tyr Leu Gly Leu Ser Cys Val Phe Ile Val Phe Leu Leu Lys Gly
1               5                   10                  15

Val Gln Ser Glu Val Lys Leu Glu Glu Ser Gly Gly Gly Leu Val Gln
            20                  25                  30

Pro Gly Gly Ser Met Lys Leu Ser Cys Val Ala Ser Gly Phe Thr Phe
        35                  40                  45

Ser Asn Tyr Trp Met Asn Trp Val Arg Gln Ser Pro Glu Lys Gly Leu
    50                  55                  60

Glu Trp Val Ala Glu Ile Arg Leu Arg Ser Ser Tyr Tyr Ala Thr His
65                  70                  75                  80

Tyr Ala Glu Ser Val Lys Gly Arg Phe Thr Ile Ser Arg Asp Asp Ser
                85                  90                  95

Lys Ser Ser Val Tyr Leu Gln Met Asn Asn Leu Arg Ala Glu Asp Thr
            100                 105                 110

Gly Ile Tyr Tyr Cys Thr Met Ile Thr Thr Gly Tyr Phe Asp Val Trp
        115                 120                 125

Gly Ala Gly Thr Thr Val Thr Val Ser Ser Ala Lys Thr Thr Pro Pro
    130                 135                 140

Ser Val Tyr Pro Leu Ala
145                 150


<210> SEQ ID NO 38
<211> LENGTH: 166
<212> TYPE: PRT
<213> ORGANISM: Artificial Sequence
<220> FEATURE:
<223> OTHER INFORMATION: VL Amino Acid Sequence for VK2 (2).2

<400> SEQUENCE: 38

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Ile His Ser Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ile Thr His Ile Pro Arg Thr Phe Gly Gly Gly Thr Lys Leu
        115                 120                 125
```

```
Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys
                165


<210> SEQ ID NO 39
<211> LENGTH: 166
<212> TYPE: PRT
<213> ORGANISM: Artificial Sequence
<220> FEATURE:
<223> OTHER INFORMATION: VL Amino Acid Sequence for VK2 (2).3

<400> SEQUENCE: 39

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Ile His Ser Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ile Thr His Ile Pro Arg Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys
                165


<210> SEQ ID NO 40
<211> LENGTH: 166
<212> TYPE: PRT
<213> ORGANISM: Artificial Sequence
<220> FEATURE:
<223> OTHER INFORMATION: VL Amino Acid Sequence for VK2 (2).5

<400> SEQUENCE: 40

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Ile His Ser Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95
```

```
Leu Lys Ile Ser Arg Val Glu Ala Glu Asp Leu Gly Val Tyr Phe Cys
            100                 105                 110

Ser Gln Ile Thr His Ile Pro Arg Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Arg
                165


<210> SEQ ID NO 41
<211> LENGTH: 166
<212> TYPE: PRT
<213> ORGANISM: Artificial Sequence
<220> FEATURE:
<223> OTHER INFORMATION: VL Amino Acid Sequence for VK2 (2).6

<400> SEQUENCE: 41

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Ile His Ser Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ile Thr His Ile Pro Arg Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys
                165


<210> SEQ ID NO 42
<211> LENGTH: 166
<212> TYPE: PRT
<213> ORGANISM: Artificial Sequence
<220> FEATURE:
<223> OTHER INFORMATION: VL Amino Acid Sequence for VK2.1

<400> SEQUENCE: 42

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Ile His Ser Asn Gly Asn Thr Tyr Leu His Trp Tyr Leu Gln Lys Pro
```

```
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ile Thr His Ile Pro Arg Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys
                165


<210> SEQ ID NO 43
<211> LENGTH: 166
<212> TYPE: PRT
<213> ORGANISM: Artificial Sequence
<220> FEATURE:
<223> OTHER INFORMATION: VL Amino Acid Sequence for VK2.2

<400> SEQUENCE: 43

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Ile His Ser Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ile Thr His Ile Pro Arg Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys
                165


<210> SEQ ID NO 44
<211> LENGTH: 166
<212> TYPE: PRT
<213> ORGANISM: Artificial Sequence
<220> FEATURE:
<223> OTHER INFORMATION: VL Amino Acid Sequence for Consensus

<400> SEQUENCE: 44

Met Lys Leu Pro Val Arg Leu Leu Val Leu Met Phe Trp Ile Pro Ala
1               5                   10                  15
```

-continued

```
Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Ile His Ser Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ile Thr His Ile Pro Arg Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys
                165
```